(12) United States Patent
Ota

(10) Patent No.: US 8,950,268 B2
(45) Date of Patent: Feb. 10, 2015

(54) MATERIAL TESTING MACHINE

(71) Applicants: Kokusai Keisokuki Kabushiki Kaisha, Tokyo (JP); Toshihiko Kuwabara, Tokyo (JP)

(72) Inventor: Tomotaka Ota, Tokyo (JP)

(73) Assignee: Kokusai Kiesokuki Kabushiki Kaisha, Tokyo (JP)

( * ) Notice: Subject to any disclaimer, the term of this patent is extended or adjusted under 35 U.S.C. 154(b) by 30 days.

(21) Appl. No.: 13/897,547

(22) Filed: May 20, 2013

(65) Prior Publication Data

US 2013/0247680 A1 Sep. 26, 2013

Related U.S. Application Data

(63) Continuation-in-part of application No. PCT/JP2011/076496, filed on Nov. 17, 2011.

(30) Foreign Application Priority Data

Nov. 18, 2010 (JP) .................................. 2010-258124
Oct. 25, 2011 (JP) .................................. 2011-234264

(51) Int. Cl.
*G01N 3/00* (2006.01)
*G01N 3/08* (2006.01)
*G01N 3/12* (2006.01)

(52) U.S. Cl.
CPC .. *G01N 3/08* (2013.01); *G01N 3/12* (2013.01); *G01N 2203/0274* (2013.01)
USPC .......................................................... 73/788

(58) Field of Classification Search
CPC combination set(s) only.
See application file for complete search history.

(56) References Cited

U.S. PATENT DOCUMENTS

| 4,211,107 | A | * | 7/1980 | Sleeter et al. ................... 73/49.6 |
| 5,325,722 | A | * | 7/1994 | Malvar ............................... 73/789 |
| 2013/0104707 | A1 | * | 5/2013 | Nakagawa ....................... 82/118 |

FOREIGN PATENT DOCUMENTS

| JP | SHO 52-131081 | 10/1977 |
| JP | 2002-323419 | 11/2002 |
| JP | 2004-205248 | 7/2004 |

OTHER PUBLICATIONS

Shunsuke Yamagishi and Toshihiko Kuwahara, "Evaluation for forming limit of steel tube by servo-controlled tube bulge test apparatus for large strain", Heisei 22 Nendo, The Proceedings of the Japanese Spring Conference for the Technology of Plasticity, May 14, 2010, pp. 193-194.
Toshihiko Kuwabara, "Advanced Material Modeling for Large Strain Using a Tube Hydro-Bulging Test Apparatus", http://www.tuat.ac.jp/~seeds/jseeds/07seedstext/093-0185/parts/o185.pdf, searched Nov. 8, 2011, pp. 186-186.
International Search Report, International Application No. PCT/JP2011/076496, Mailed: Jan. 17, 2012.

* cited by examiner

*Primary Examiner* — Lisa Caputo
*Assistant Examiner* — Brandi N Hopkins
(74) *Attorney, Agent, or Firm* — McCarter & English, LLP

(57) ABSTRACT

A material testing machine measuring strain of a tube-like test piece, comprising: a plurality of radial direction displacement detection units; an axis direction displacement detection unit; and a calculation unit that calculates the strain, wherein: each of first and second displacement meters of at least one of the radial direction displacement detection units comprises: a needle; a fixed frame; a movable frame; and a displacement sensor having a body part and a contact protruding from the body part, and wherein a tip of the contact contacts a stopper plate; the needle is oriented in the radial direction of the test piece; the needle protrudes from an end of the movable frame; displacement in the radial direction of the test piece is detected by detecting a moving amount of the needle; and the calculation unit calculates a curvature radius in the tube axis direction of the test piece.

10 Claims, 13 Drawing Sheets

MATERIAL TESTING MACHINE

This is a Continuation-in-Part of International Application No. PCT/JP2011/076496 filed Nov. 17, 2011, which claims priority from Japanese Patent Applications Nos. 2010-258124 filed Nov. 18, 2010 and 2011-234264 filed Oct. 25, 2011. The entire disclosure of the prior applications is hereby incorporated by reference herein its entirety.

TECHNICAL FIELD

The present invention relates to a material testing machine that test a mechanical property of a material by applying a tensile stress or a compressive stress to a test piece, and particularly to a tube bulge testing machine where a biaxial stress testing is performed while applying an inner pressure and an axis force to a tube-like test piece.

BACKGROUND

In order to realize high-precision press molding simulation, high-precision material property evaluation by a multi-axis stress testing is required. It is known that an liquid pressure bulge testing is effective for material property evaluation particularly for a large strain area. In non-patent document 1 ("Advanced material modeling for large strain using a tube hydro-bulging test apparatus", Toshihiko Kuwabara, <URL: http://www.tuat.ac.jp/~seeds/j seeds/07seedstext/093-0185/parts/0185.pdf> (searched on Nov. 8, 2011)), an axial-force-inner pressure type tube bulge testing machine (hereafter, referred to as a "tube bulge testing machine") which performs an liquid pressure bulge testing while applying an inner pressure and an axial force to a tube-like test piece is disclosed. In the tube bulge testing, a central portion in a tube axis direction of a test piece expands (in a circumferential direction and a tube axis direction), and a vertical cross section of the test piece forms a bulge vertex in a shape of a bell. Based on an outer diameter, a wall thickness, a curvature radius in the tube axis direction and a testing load (inner pressure and axial force), the stress in two directions including the circumferential direction and the tube axis direction are obtained.

SUMMARY

However, a test piece is not completely symmetrical with respect to a tube axis, and the wall thickness or the outer diameter varies depending on a direction (a direction around the tube axis). Therefore, change in shape of the bulge apex becomes asymmetrical with respect to the tube axis. Conventionally, since the outer diameter of the test piece is measured only in one direction, measurements of the outer diameter vary and the measurement precision of strain of the test piece was low.

The present invention is advantageous in that it provides a material testing machine capable of performing high-precision axial force-inner pressure type tube bulge testing without using a strain gauge for measuring deformative action of a test piece.

According to an aspect of the invention, there is provided a material testing machine measuring strain of a tube-like test piece by applying inner pressure and stress in a tube axis direction to the test piece, comprising: a plurality of radial direction displacement detection units that detect displacements of an outer circumferential surface of the test piece in a radial direction in a central portion of an effective length of the test piece; an axis direction displacement detection unit that detects a displacement in the tube-axis direction of the outer circumferential surface of the test piece in the central portion of the effective length of the test piece; and a calculation unit that calculates the strain in a circumferential direction and the tube-axis direction of the test piece in the central portion of the effective length, based on detection results by the plurality of radial direction displacement detection units and the axis direction displacement detection unit. The plurality of radial direction displacement detection units respectively detect displacements at different directions around the tube axis of the test piece. Each of plurality of radial direction displacement detection units comprises a first displacement meter that detects a displacement in the radial direction of the outer circumferential surface of the test piece in the central portion of the effective length. At least one of the plurality of radial direction displacement detection units comprises a second displacement meter that is aligned with the first displacement meter in the tube axis direction and detects a displacement in the radial direction of the outer circumferential surface of the test piece. Each of the first and second displacement meters comprises: a needle that has a tip arranged to perpendicularly contact the outer circumferential surface of the test piece and is provided to be able to move in the radial direction in accordance with the displacement in the radial direction of the outer circumferential surface of the test piece; a fixed frame; a movable frame that is provided to be able to move in the radial direction of the test piece with respect to the fixed frame; and a displacement sensor that has a body part attached to the movable frame and a contact that protrudes from an end of the body part in the radial direction of the test piece in a retractable manner. A tip of the contact of the displacement sensor is arranged to contact a stopper plate provided on the fixed frame. The needle is arranged such that a lengthwise direction is oriented in the radial direction of the test piece. The needle is attached to the movable frame such that the needle protrudes from an end of the movable frame facing the test piece. The displacement in the radial direction of the circumferential surface of the test piece is detected by detecting a moving amount of the needle. The calculation unit calculates a curvature radius in the tube axis direction of the outer circumferential surface of the test piece in the central portion of the effective length, based on detection results by the first and second displacement meters of the at least one of the plurality of radial direction displacement detection units.

With this configuration, variations of measurements of an outer diameter of a test piece can be decreased to a low level, and it becomes possible to measure the strain of the test piece with a high degree of precision.

The plurality of radial direction displacement detection units may comprise first, second and third radial direction displacement detection units arranged around the tube axis of the test piece at intervals of 120°.

The material testing machine may further comprise a sensor unit moving mechanism that moves a sensor unit, in which the plurality of radial direction displacement detection units and the axis direction displacement detection unit are provided, in the tube axis direction of the test piece with respect to a device frame of the material testing machine. In this case, the sensor unit moving mechanism may comprise: a first movable part that is provided to be able to move in the tube axis direction of the test piece with respect to the device frame and comprises a movable chuck which fixes one end of the test piece; a fixed part that is fixed to the device frame and comprises a fixed chuck which fixes the other end of the test piece; a second movable part that is arranged between the first movable part and the fixed part and moves the sensor unit in the tube axis direction of the test piece with respect to the device frame; and an actuator that is fixed to the device frame and moves the first movable part in the tube axis direction; and a link mechanism that couples the device frame, the first movable part and the second movable part with each other, and moves a central measuring device to a midway point between the movable chuck and the fixed chuck in accordance with movement of the first movable part.

According to another aspect of the invention, there is provided a material testing machine measuring a response of a test piece by applying a stress to the test piece in a predetermined direction, comprising: a device frame; a first movable part that is provided to be able to move in the predetermined direction with respect to the device frame and comprises a movable chuck which fixes one end of the test piece; a fixed part that is fixed to the device frame and comprises a fixed chuck which fixes the other end of the test piece; a second movable part that is provided between the first movable part and the fixed part to be able to move in the predetermined direction with respect to the device frame and comprises a central measuring device which measures the response of the test piece in a central portion in the predetermined direction of the test piece when a load acts on the test piece; an actuator that is fixed to the device frame and moves the first movable part in the tube axis direction; a link mechanism that couples the device frame, the first movable part and the second movable part with each other, and keeps the central measuring device at a midway point of the test piece in the predetermined direction by moving the central measuring device to a midpoint between the movable chuck and the fixed chuck in accordance with movement of the first movable part; and a rail that extending in the predetermined direction. The first movable part comprises a first runner block which engages with the rail, and is supported by the rail and the first runner block to be able to slide in the predetermined direction. The second movable part comprises a second runner block that engages with the rail, and is supported by the rail and the second runner block to be able to slide in the predetermined direction.

The fixed part may comprise: a load sensor that measures a load acting on the test piece in the predetermined direction; and a third runner block that engages with the rail to be able to move in the predetermined direction. The fixed chuck may be located on the third runner block, and is fixed to the device frame via the load sensor.

The link mechanism may comprise: a first link whose one end is rotatably coupled to the first movable part via a first pin; a second link whose one end is rotatably coupled to the second movable part via a second pin; and a third link whose one end is rotatably coupled to the device frame via a third pin arranged on an opposite side of the first pin with respect to the second pin. In this case, the other end of the first link and the other end of the third link is rotatably coupled via a fourth pin. The other end of the second link is rotatably coupled to one of the first link and the third link via a fifth pin. An interval between the fourth pin and the first pin is equal to an interval between the fourth pin and the third pin. An interval between the fifth pin and the second pin is equal to an interval between the fifth pin and one of the first pin and the third pin provided for one of the first link and the third link on which the fifth pin is provided.

The first movable part, the second movable part and the fixed part may comprise base plates having lower surfaces on which the first, second and third runner blocks are attached, respectively. The movable chuck, the central measuring device and the fixed chuck may be respectively attached to upper surfaces of the base plates of the first movable part, the second movable part and the fixed part, and may be respectively arranged above the base plates of the first movable part, the second movable part and the fixed part. The link mechanism may be attached to lower surfaces of the base plates and may be located under the base plates.

The device frame may comprise a plate having a horizontally oriented upper surface. The rail may be attached to the upper surface of the device frame. The plate may have a recessed part which is recessed in a horizontal direction by cutting off a central portion on a side of the plate. The recessed part may have a bottom surface extending in parallel with and adjacent to the rail. The first link and the third link may be arranged in the recessed part.

According to another aspect of the invention, there is provided a material testing machine measuring strain of a tube-like test piece by applying inner pressure and stress in a tube axis direction to the test piece, comprising: a plurality of radial direction displacement detection units that detect displacements of an outer circumferential surface of the test piece in a radial direction in a central portion of an effective length of the test piece; an axis direction displacement detection unit that detects a displacement in the tube-axis direction of the outer circumferential surface of the test piece in the central portion of the effective length of the test piece; and a calculation unit that calculates the strain in a circumferential direction and the tube-axis direction of the test piece in the central portion of the effective length, based on detection results by the plurality of radial direction displacement detection units and the axis direction displacement detection unit. The plurality of radial direction displacement detection units respectively detect displacements at different directions around the tube axis of the test piece. The axis direction displacement detection unit comprises: a fixed plate; a movable plate provided to be able to slide in a Z-axis direction with respect to the fixed plate; and a body unit that is provided at a tip portion in the Z-axis direction of the movable plate to be able to swing about a Y-axis. The body unit comprises: a plate attached to the movable plate to be able to swing; a first sliding part that has a first jaw provided to contact a side of the test piece and is provided to be able to slide in the X-axis direction with respect to the plate; a second sliding part that has a second jaw provided to contact a side of the test piece and is provided to be able to slide in the X-axis direction with respect to the plate; and a contact-type displacement meter that detects a relative displacement in the X-axis direction between the first jaw and the second jaw.

According to another aspect f the invention there is provided a material testing machine measuring a response of a test piece by applying a stress to the test piece in a predetermined direction, comprising: a device frame; a first movable part that is provided to be able to move in the predetermined direction with respect to the device frame and comprises a movable chuck which fixes one end of the test piece; a fixed part that is fixed to the device frame and comprises a fixed chuck which fixes the other end of the test piece; a second movable part that is provided between the first movable part and the fixed part to be able to move in the predetermined direction with respect to the device frame and comprises a central measuring device which measures the response of the test piece in a central portion in the predetermined direction of the test piece when a load acts on the test piece; an actuator that is fixed to the device frame and moves the first movable part in the tube axis direction; and a link mechanism that couples the device frame, the first movable part and the second movable part with each other, and keeps the central measuring device at a midway point of the test piece in the predetermined direction by moving the central measuring device to a midpoint between the movable chuck and the fixed chuck in accordance with movement of the first movable part.

The link mechanism comprises: a first link whose one end is rotatably coupled to the first movable part via a first pin; a second link whose one end is rotatably coupled to the second movable part via a second pin; and a third link whose one end is rotatably coupled to the device frame via a third pin arranged on an opposite side of the first pin with respect to the second pin. The other end of the first link and the other end of the third link is rotatably coupled via a fourth pin. The other end of the second link is rotatably coupled to one of the first link and the third link via a fifth pin. An interval between the fourth pin and the first pin is equal to an interval between the fourth pin and the third pin. An interval between the fifth pin and the second pin is equal to an interval between the fifth pin and one of the first pin and the third pin provided for one of the first link and the third link on which the fifth pin is provided.

DETAILED DESCRIPTION OF EMBODIMENTS

Figure 1:
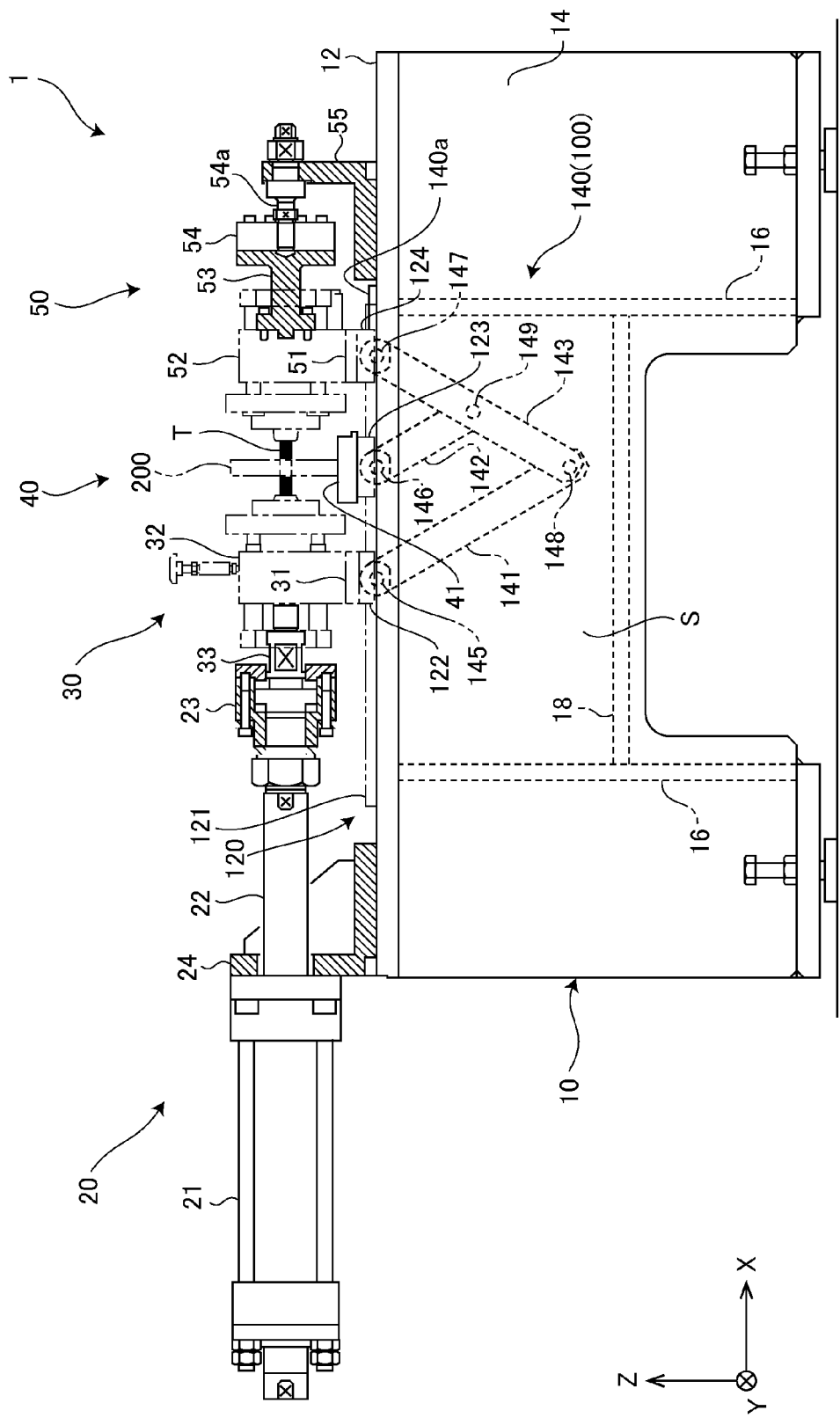
FIG. 1 is a front view of a material testing machine according to an embodiment of the invention.
Figure 2:
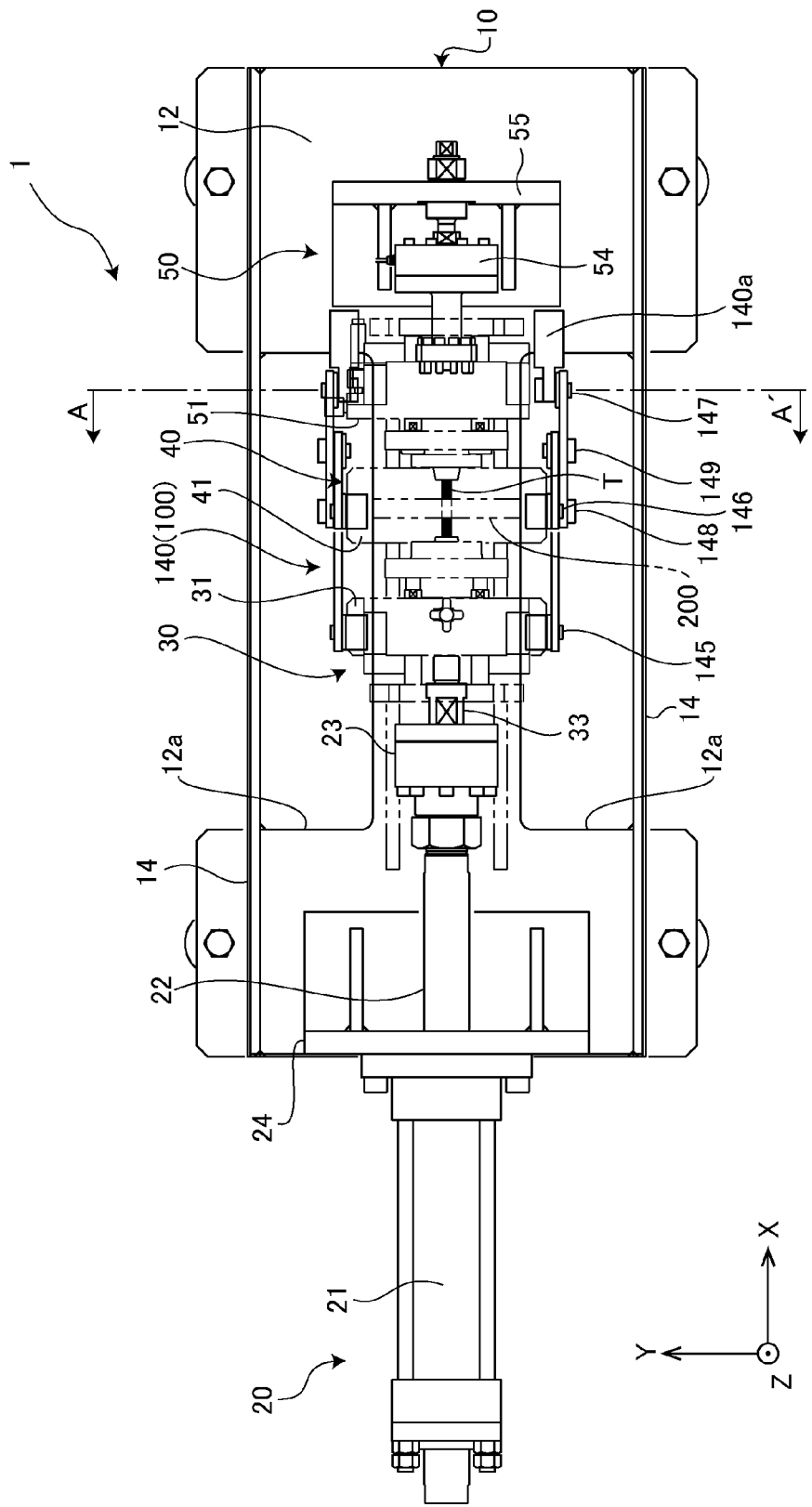
FIG. 2 is a top view of the material testing machine according to the embodiment of the invention.
Figure 3:
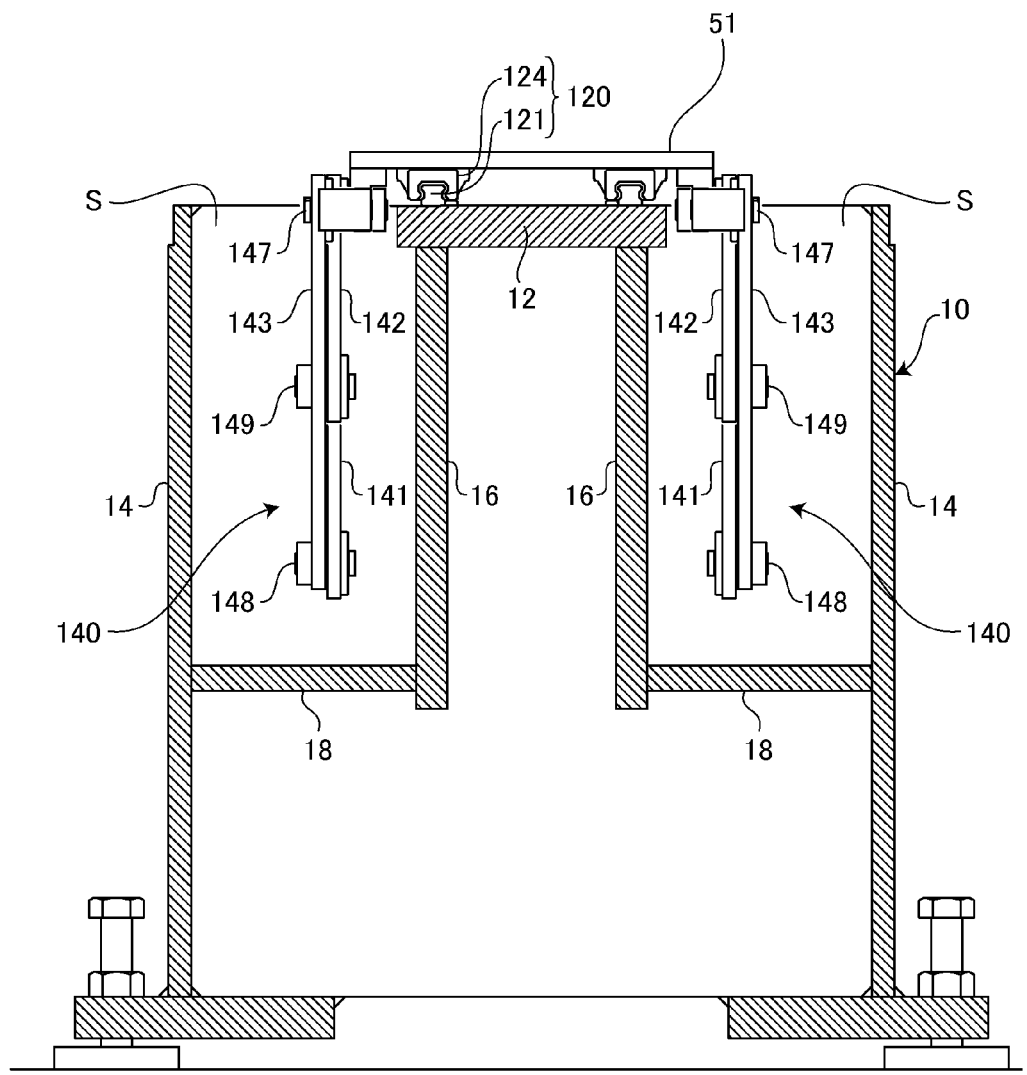
FIG. 3 is a fragmentary sectional view taken in the direction of an arrow A-A in FIG. 2.

Hereafter, an embodiment of the invention is described with reference to the accompanying drawings. A material testing machine 1 according to the embodiment of the invention is configured to perform an axial force-internal pressure type circular tube bulge testing for measuring an elasto-plasticity action of a tube-like test piece T while applying an internal pressure and an axial force to the tube-like test piece T. FIGS. 1 and 2 are a front view and a top view of the material testing machine 1, respectively. FIG. 3 is a fragmentary sectional view taken in the direction of an arrow A-A in FIG. 2, and shows only a frame 10 and a sensor unit moving mechanism 100 described later. In the following explanations, a left and right direction in FIG. 1 is defined as an X-axis direction (a right direction is a positive direction in X-axis), a direction perpendicular to a paper face on FIG. 1 is defined as a Y-axis direction (a direction pointing from the front side to the back side of the paper face is defined as a positive direction in the Y-axis direction), the up and down direction in FIG. 1 is defined as a Z-axis direction (a upper direction is a positive direction in Z-axis). Furthermore, the up and down direction (Y-axis direction) in FIG. 2 is defined as a "depth direction", and an upper side and a lower side are respective referred to as a "rear" side and a "front" side, respectively.

The material testing machine 1 includes the frame 10, an oil pressure cylinder 20, a first movable part 30, a second movable part 40, a fixed part 50, and the sensor unit moving mechanism 100, and an oil pressure source, a liquid pressure source and a control unit not shown. The oil pressure source is a device which supplies an oil pressure for driving the oil pressure cylinder 20, and the liquid pressure source is a device which supplies pressurized liquid (e.g., water mixed with a rust preventive agent) to the inside of a tube of the test piece T. The frame 10 is a base frame which supports each part of the material testing machine 1, and each part of the material testing machine 1 excepting the oil pressure source, the liquid pressure source and the control unit is fixed to a base plate 12 provided on the upper surface of the frame 10. In a central portion in the X-axis direction of the base plate 12, recessed parts 12a, each of which has a rectangular shape, are formed on the front side and the rear side respectively, and in the top view (FIG. 2) the base plate 12 has an outer shape of a letter "H". The frame 10 has a pair of outer walls 14 covering the both sides in the depth direction of the frame 10, a pair of inner walls 16 each of which has a horizontal cross sectional surface having a shape of a letter "U" and vertically extending from the lower surface of the periphery of each recessed part 12a of the base plate 12, and a pair of horizontally aligned bottom plates 18 covering a pair of inner spaces S surrounded by the inner walls 16 and the outer walls 14.

Figure 4:
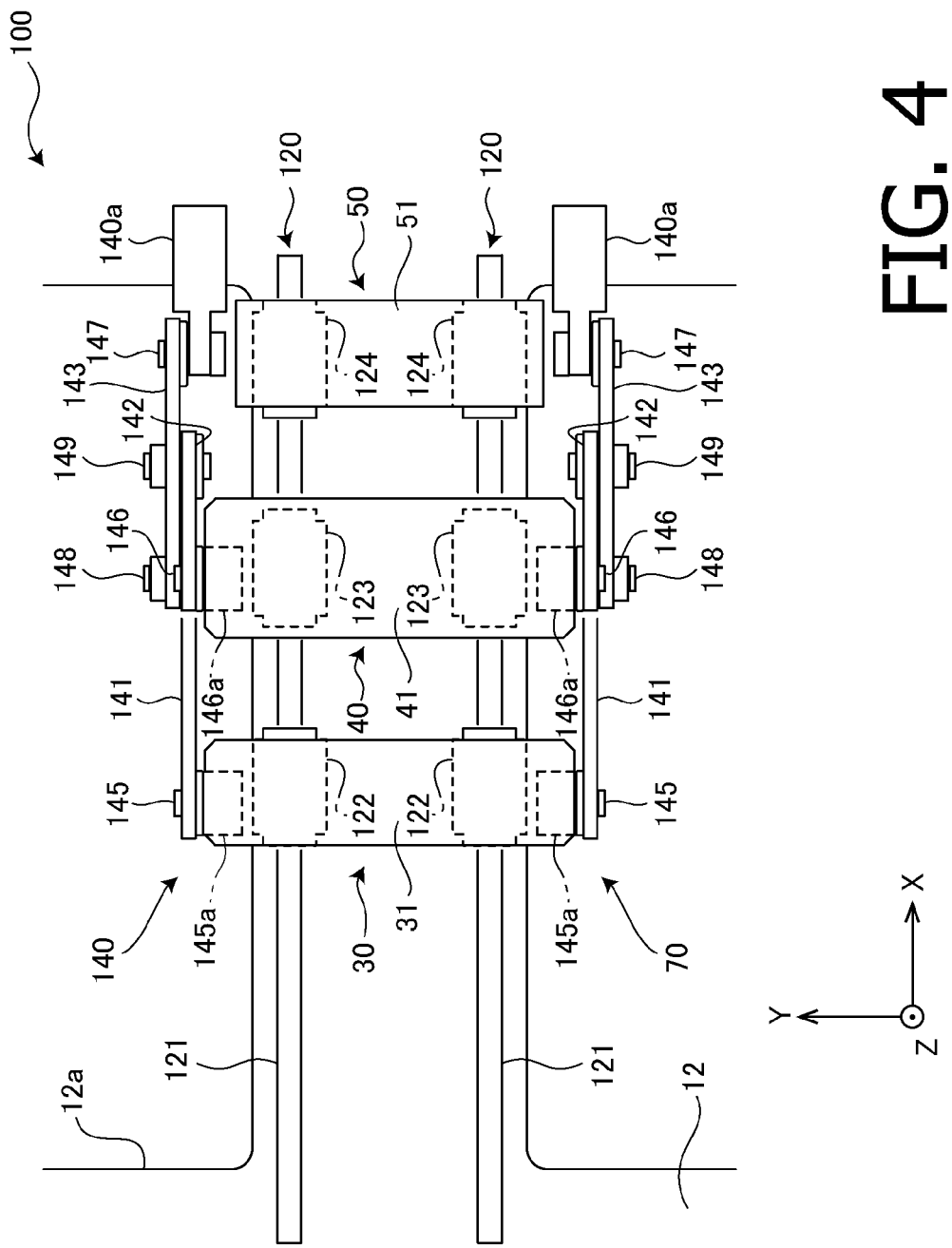
FIG. 4 is a top view of a sensor unit moving mechanism.

FIG. 4 is a top view of the sensor unit moving mechanism 100. The sensor unit moving mechanism 100 is configured to move the second movable part 40 in accordance with movement of the first moving part 30 so that the second movable part 40 (i.e., a sensor unit 200) is precisely located at an intermediate point between the first movable part 30 and the fixed part 50. The sensor unit moving mechanism 100 is provided with two linear guides 120 and two link mechanisms 140. Each linear guide 120 includes a rail 121 and three runner blocks 122, 123 and 124 which engage with the rail 121 to be movable along the rail 121. The rails 121 of the two linear guides 120 are arranged between the pair of recessed parts 12a respectively formed in the base plate 12. That is, the two rails 121 extending in the X-axis direction are arranged to have a certain interval in the Y-axis direction to be parallel with each other, and are fixed to the upper surface of the base plate 12. The first movable part 30 and the second movable part 40 are respectively attached to the runner blocks 122 and 123 of each linear guide 120, and the first movable part 30 and the second movable part 40 are provided to be smoothly movable in the X-axis direction by the linear guide 120. To each runner block 124, a chuck 52 (described later) of the fixed part 50 is attached. The runner blocks 122, 123 and 124 are coupled to each other by the link mechanism 140, and even when the runner block 122 moves, the runner block 123 is constantly and precisely located at an intermediate point between the runner blocks 122 and 124. Details of the link mechanism 140 is described later. On the base plate 12, an unshown linear encoder which detects the position of the runner block 122 is provided. The linear encoder is communicably connected to the control unit, and position information (i.e., position information of the chuck 32 described later) of the first movable part 30 detected by the linear encoder during testing is sent to the control unit, and is recorded in a recording device of the control unit.

The oil pressure cylinder 20 is an oil pressure type direct acting actuator driven in the X-axis direction by the oil pressure supplied from the oil pressure source not shown. A cylinder tube 21 of the oil pressure cylinder 20 is fixed to a negative side end in the X-axis direction of the base plate 12 via a bracket 24. From a positive side end of the cylinder tube 21, a piston rod 22 capable of moving in the X-axis direction protrudes. At a tip of the piston rod 22, an attachment 23 which couples the piston rod 22 with the chuck 32 is provided.

The first movable part 30 includes a base 31, the chuck (movable chuck) 32 and a joint member 33. The runner blocks 122 of the linear guides 120 are attached to both ends in the depth direction of the lower surface of the base 31. To the upper surface of the base 31, the chuck 32 which holds an end of the test piece T is attached. Therefore, a relatively large weight of the chuck 32 is supported by the base 31 and the two linear guides 120 to be slidable in the X-axis direction. Furthermore, the back side of the chuck 32 (the left side in FIG. 1) is fixed to the attachment 23 of the oil pressure cylinder 20 via the joint member 33, and the chuck 32 is driven in the X-axis direction in accordance with movement of the piston rod 22. Thanks to the above described configuration in which the relatively large weight of the chuck 32 is slidably supported by the linear guide 120, no bending moment is applied to the oil pressure cylinder 20 and the smooth and precise driving in the X-axis direction by the oil pressure cylinder 20 can be realized. Furthermore, no undesired bending moment is applied to the test piece T, and a precise testing can be realized.

The second movable part 40 includes a base 41 and the sensor unit 200. The runner blocks 123 of the linear guides 120 are attached to both ends in the depth direction of the lower surface of the base 41. To the upper surface of the base 41, the sensor unit 200 which measures the shape of the central portion in the lengthwise direction of the test piece T (the X-axis direction) is attached. The details of the sensor unit 200 are described later.

The fixed part 50 includes a base 51, a chuck (fixed chuck) 52, a joint member 53, a load cell 54 and a bracket 55. To the upper surface of the base 51, the chuck 52 which holds the other end of the testing piece T is attached. The runner blocks 124 of the linear guides 120 are attached at both ends in the depth direction of the lower surface of the base 51. Therefore, a relatively large weight of the chuck 52 is supported by the base 51 and the two linear guides 120 to be slidable in the X-axis direction. Furthermore, to the back side of the chuck 52 (the right side in FIG. 1), an attachment seating of the load cell 54 is attached via the joint member 53. A load-support bar 54a vertically protrudes from a load-support plate for the load cell 54 (a right side plate in FIG. 1), and the load-support bar 54a is fixed to the bracket 55 attached to the base plate 12. By the load cell 54 thus arranged, the testing load (axial force) applied in the X-axis direction to the testing pieces T is detected. Thanks to the above described configuration in which the relatively large weight of the chuck 52 is slidably supported by the linear guide 120, a large bending moment is not applied to the load cell 54, and thereby precise measurement of the axial force by the load cell 54 can be realized. Furthermore, since the chuck 52 is able to move on the linear guide 120 in the X-axis direction with a low degree of resistance, the axial force acting on the chuck 52 is transmitted to the load cell 54 with almost no loss, and is detected precisely by the load cell 54. Furthermore, the load cell 54 is connected to the control unit, and a detection signal (a resistance value by a strain gauge) is read by a known bridge circuit provided in the control unit and is converted into testing load data. The information on the testing load detected by the load cell 54 during the testing is associated with position information of the first movable part 30 detected concurrently, and is stored in a memory of the control unit.

Next, the link mechanism 140 is explained with reference to FIGS. 1, 3 and 4. In this embodiment, two link mechanisms 140, each of which is vertically arranged, are provided in the inner space S of the frame 10. Since structures of the two link mechanisms 140 are in the mirrored image relationship, explanation thereof is made only for the structure of the forehand link mechanism 140.

The link mechanism 140 includes three long plate-like links (movable links) 141, 142 and 143 rotatably coupled to each other by pins, and a fixed link 140a fixed to the upper surface of the base plate 12. At both ends of each movable link, joint holes for letting pins pass therethrough are formed. At an end of the fixed link 140a, a joint hole is formed. In the movable link 143, a third joint hole is formed at the center between the joint holes at the both ends. In the joint hole of one of the coupled two links, a bearing for rotatably holding the pin is provided. With this configuration, the links are coupled to be smoothly roatable with respect to each other. The links 141 and 143 are members having the same link length 2L (an interval between the joint holes provided at the both ends), and the link 142 has the link length L which is half of the 2L.

As shown in FIG. 4, at both ends in the depth direction of the bases 31 and 41, the pins 145 and 146 are fixed by pin fixing member 145a and 146a, respectively. The pin 145 is inserted into a joint hole at one end of the link 141, and the link 141 is rotatably coupled to the base 31 via the pin 145. Similarly, the link 142 is rotatably coupled to the base 41 via the pin 146. One end of the link 143 is rotatably coupled to one end of the fixed link 140a via the pin 147. The other end of the link 141 is rotatably coupled to the other end of the link 143 via a pin 148. The other end of the link 142 is rotataby coupled to the center portion of the link 143 via the pin 149.

As described above, since the link lengths of the links 141 and 143 are the same, a triangle whose vertexes are defined at the pins 145, 147 and 148 (hereafter, referred to as an "isosceles triangle 578") is an isosceles triangle. The link length of the link 142 is half of the link length of the link 143, and the joint hole of the other end of the link 142 is coupled by the pin 149 to the joint hole at the center in the lengthwise direction of the link 143. Therefore, by connecting the pins 146, 147 and 149, an isosceles triangle (hereafter, referred to as an "isosceles triangle 679") is formed. The isosceles triangles 578 and 679 are similar to each other at the similitude ratio of 2:1. Therefore, even when the first movable part 30 (the pin 145) moves, the pin 146 is always situated at the midway point between the pins 145 and 147. That is, when the first movable part 30 moves in the X-axis direction by being driven by the oil pressure cylinder 20, the link mechanism 140 coupled to the first movable part 30 by the pin 145 acts, and the second movable part 40 coupled to the link mechanism 140 by the pin 146 moves to the midway point between the fixed part 50 and the moved first movable part 30. The pins 145, 146 and 147 are attached to reference positions in the X-axis direction (the X-axis reference points) of the first movable part 30, the second movable part 40 and the fixed part 50 (specifically, the bases 31, 41 and 51), respectively. When the test piece T is attached to the material testing machine 1, substantial end parts (ends of a deformable part which is not clamped by the chuck) of the test piece T are attached to the X-axis reference points of the first movable part 30 and the fixed part 50. Therefore, to the X-axis reference point of the second movable part 40, the midway point of a span of the test piece T (the midway point in an effective length of the test piece T) is situated. The sensor unit 200 provided in the second movable part 40 is configured to measure the shape of the test piece T at the X-axis reference point of the second movable part 40. Therefore, even if the length of the test piece T is changed by a testing load during the testing, it is possible to constantly measure the shape of the substantial central portion of the test piece T in the length direction by the sensor unit 200.

Figure 5:
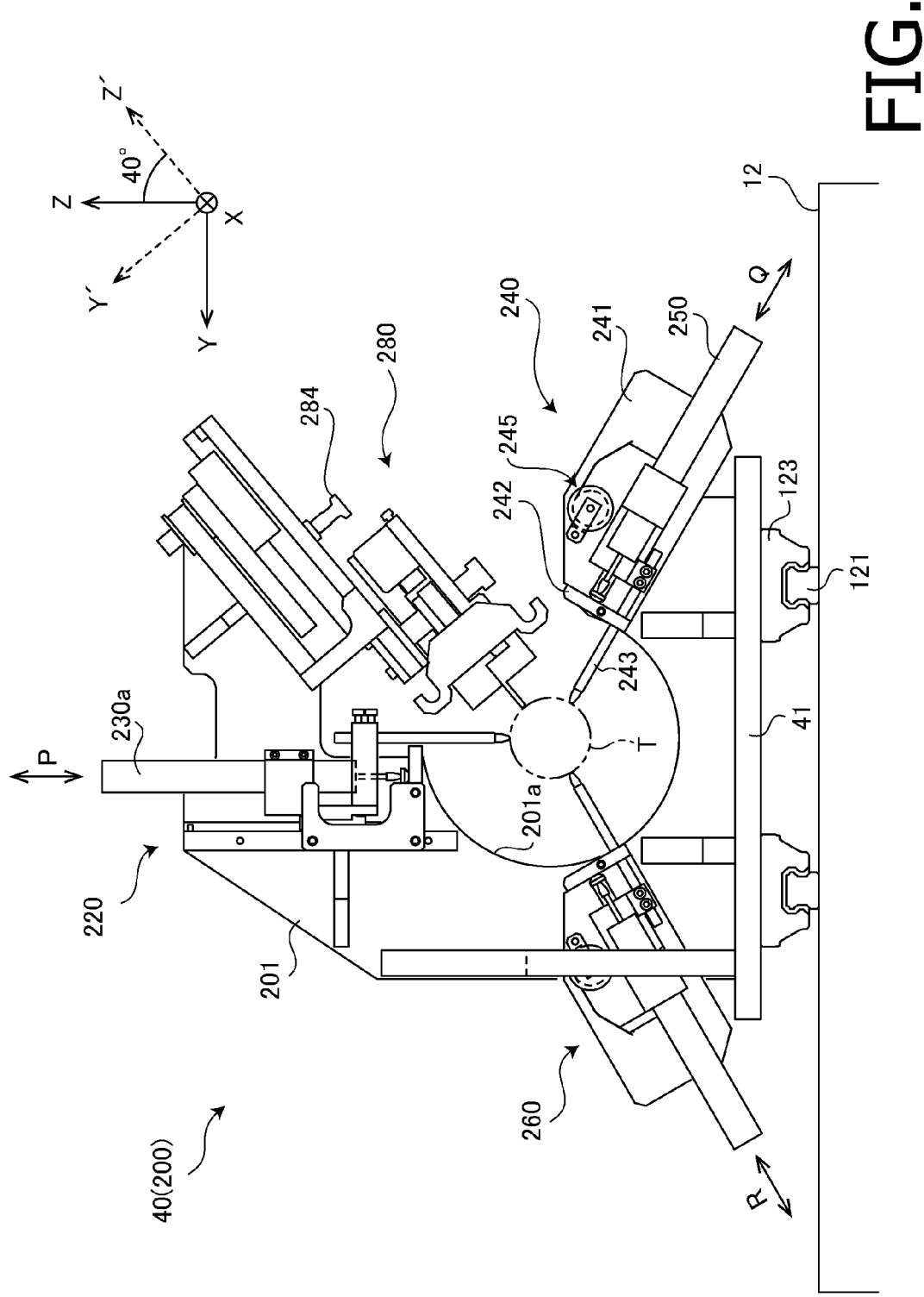
FIG. 5 is a side view of the sensor unit moving mechanism.
Figure 6:
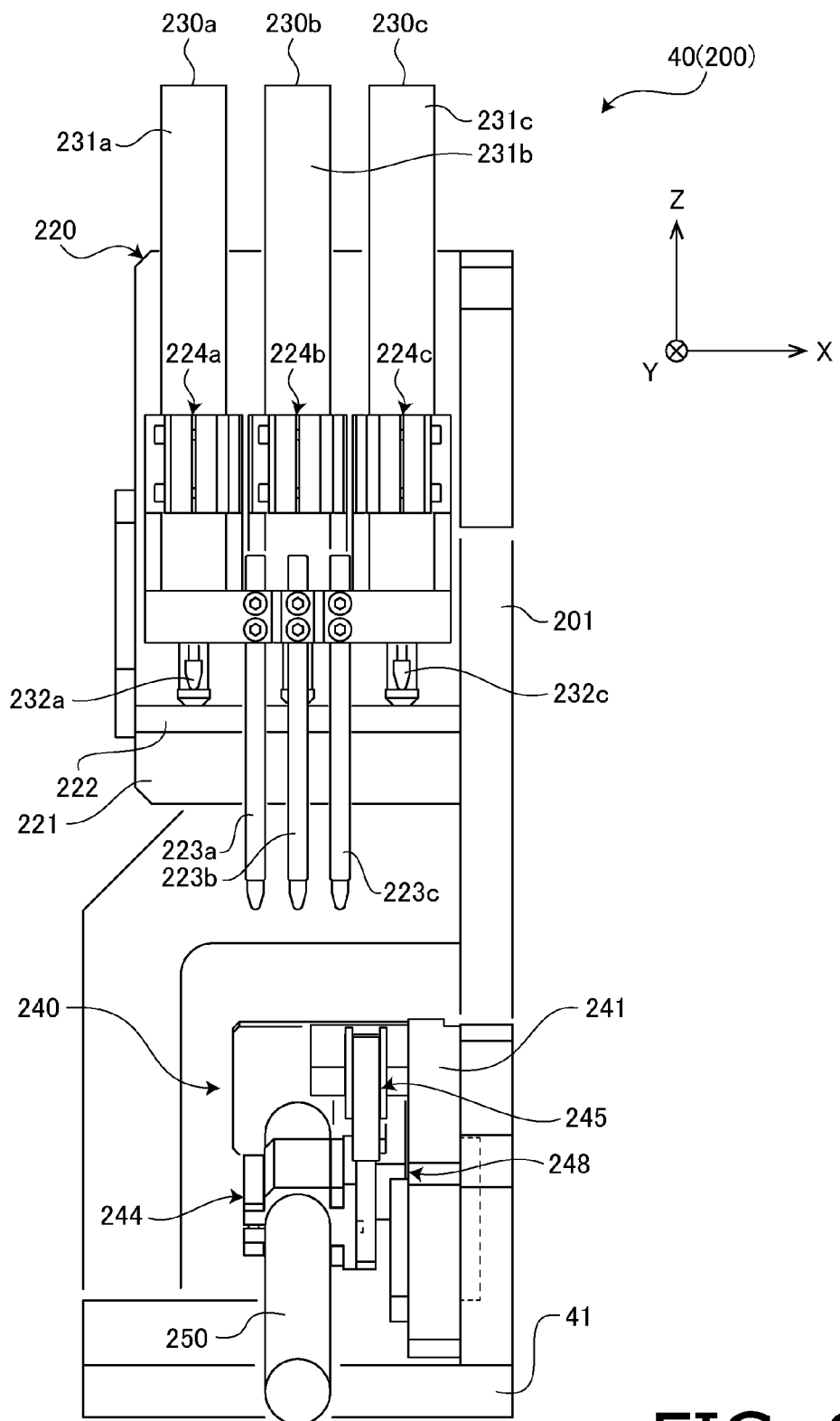
FIG. 6 is a front view of the sensor unit moving mechanism.

Next, the sensor unit 200 according to the embodiment of the invention is explained. The sensor unit 200 is constantly situated at the midway point between the movable chuck 32 and the fixed chuck 52 by the above described sensor unit moving mechanism 100, and is a component for measuring displacement of the test piece T in the lengthwise and radial directions thereof at the central portion in the span of the test piece T. FIG. 5 is a drawing illustrating the second movable part 40 to which the sensor unit 200 is attached, viewed along the X-axis direction. FIG. 6 is a drawing illustrating the sensor unit 200, viewed along the Y-axis direction (i.e., viewed from the front side of the material testing machine 1). The sensor unit 200 includes a plate 201, a first radial direction displacement detection unit 220, a second radial direction displacement detection unit 240, a third radial direction displacement detection unit 260 and an axis direction displacement detection unit 280. The plate 201 is a flat plate vertically expanding from an end of the base 41 in the X-axis direction, and an opening 201a having a periphery in an arc shape is formed in the central portion of the plate 201 and the test piece T is inserted into the opening 201a. The opening 201a is formed such that the upper side thereof (an upper right portion in FIG. 5) is opened and that the test piece T can be inserted into and drawn from the inside of the opening 201a via the opened portion.

The first, second and third radial direction displacement detection units 220, 240 and 260 and the axis direction displacement detection unit 280 are attached to a surface of the plate 201 (a front side of the paper surface of FIG. 5). The first, second and third radial direction displacement detection units 220, 240 and 260 are arranged around the axis of the test piece T to have angular intervals of 120°. Furthermore, the first radial direction displacement detection unit 220 is arranged just above the test piece T.

Figure 7:
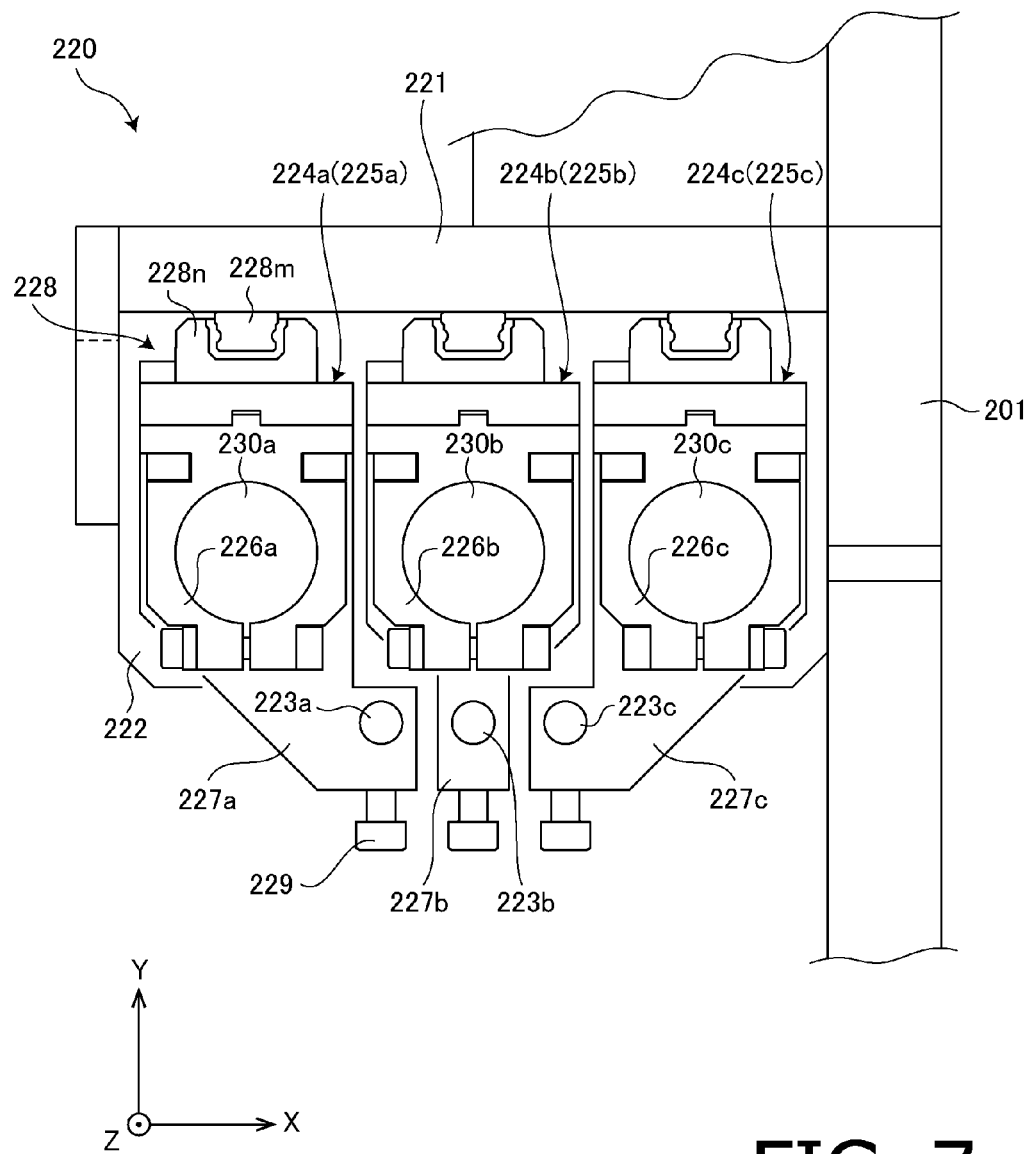
FIG. 7 is a top view of a first radial direction displacement detection unit.

FIG. 7 illustrates the first radial direction displacement detection unit 220 viewed from the upper side. As shown in FIGS. 6 and 7, the first radial direction displacement detection unit 220 includes a plate 221, three contact-type displacement meters 230a to 230c, three needles 223a to 223c, sensor support members 224a to 224c which fix the needles 223a to 223c to bodies 231a to 231c of the contact-type displacement meters 230a to o230c, and three linear guides 228 which supports the bodies 231a to 231c of the contact-type displacement meters and the needles 223a to 223c to be slidable in the vertical direction (Z-axis direction) with respect to the plate 221.

The contact-type displacement meters 230a to 230c include the bodies 231a to 231c each having a shape of a column, and contacts 232a to 232c each having a shape of a round bar. In each of the bodies 231a to 231c, a circular hole is formed to extend along the center axis from one end, and the contacts 232a to 232c are respectively accommodated in the circular holes to be slidable in the center axis direction. Furthermore, the contacts 232a to 232c are pressed toward the tip side by coil springs (not shown) which are respectively provided in the bodies 231a to 231c of the contact-type displacement meters 230a to 230c, and the tips of the contacts 232a to 232c protrude from the ends of the bodies 231a to 231c, respectively. The contact-type displacement meters 230a to 230c detect the positions and displacements of the contacts 232a to 232c in the center axis direction (a measurement axis direction P) with respect to the bodies 231a to 231c, respectively.

The plate 221 is a support frame arranged to protrude from the surface (the surface on the negative side of X-axis) of the plate 201 and to be parallel with the test piece T. On a surface of the plate 221 (a surface on the negative side of Y-axis), rails 228m of the three linear guides 228 arranged to have the same intervals in X-axis direction are fixed to extend in the Z-axis direction. A runner block 228n engages with the rail 228m to be slidable along the rail 228m. To attachment surfaces of the runner blocks 228n, plates 225a to 225c of the sensor support members 224a to 224c are attached. Furthermore, to the sides of the plates 225a to 225c opposite to the runner blocks 228n, clamps 226a to 226c for attaching the bodies 231a to 231c of the contact type displacement meters are attached. By attaching the bodies 231a to 231c to the clamps 226a to 226c, respectively, the bodies 231a to 231c are supported by the plate 221 (i.e., the frame of the sensor unit 200) to be sladable in the measurement axis direction P.

From lower edges of the plates 225a to 225c, arms 227a to 227c extend horizontally to the negative side of Y-axis. In the tip portions of the arms 227a to 227c, through holes into which the needles 223a to 223c are inserted are formed to extend in Z-axis direction. The needles 223a to 223c are fixed to the arms 227a to 227c by screws 229 in the state where the needles 223a to 223c protrude by a predetermined length from the lower surfaces of the arms 227a to 227c. As a result, the needles 223a to 223c are fixed to be parallel with the bodies 231a to 231c of the contact-type displacement meters, and are supported to be slidable in Z-axis direction (i.e., the measurement axis direction P) together with the bodies 231a to 231c of the contact-type displacement meters.

The needles 223a to 223c are arranged perpendicularly to the center axis (X-axis) of the tube-like test piece T (in parallel with Z-axis), and are arranged in the X-axis direction to have the same intervals (intervals of 10 mm in this embodiment). Furthermore, the center needle 223b is precisely located at the X-axis reference point of the second movable part 40, and the tip thereof contacts the center in the span of the test piece T.

From a portion near the lower edge of the surface of the place 221, a stopper plate 222 protrudes to the negative side in the Y-axis direction to be perpendicular to the plate 221 and to be parallel with the test piece T. The tips of the contacts 232a to 232c of the contact-type displacement meters contact the upper surface of the stopper plate 222. Since the contacts 232a to 232c are pressed to the tip side by the coil springs provided respectively in the bodies 231a to 231c of the contact-type displacement meters, the contacts 232a to 232c protrude further from the bodies 231a to 231c while the tips thereof contact the stopper plate 222 when the bodies 231a to 231c of the contact-type displacement meters move upward together with the needles 223a to 223c. As a result, the movement amounts in the Y-axis direction of the needles 223a to 223c are detected by the contact-type displacement meters 230a to 230c.

Similarly, the second radial direction displacement detection unit 240 includes a plate 241 (a stopper plate 242), a contact-type displacement meter 250, a needle 243, a sensor support member 244 which fixes the needle 243 to a body 251 of the contact-type displacement meter 250, and a linear guide 248 which supports the body 251 of the contact-type displacement meter and the needle 243 to the plate 241 to be slidable in the measurement axis direction Q of the contact-type displacement meter 250. However, the second radial direction displacement detection unit 240 includes only a set of the contact-type displacement meter 250, the needle 243, the sensor support member 244 and the linear guide 248, and the plate 241 is arranged to be parallel with the plate 201. Furthermore, in the second radial direction displacement detection unit 240, a spring mechanism 245 which presses the body 251 of the contact-type displacement meter to the test piece T side against the gravity is provided, so that the tip of the needle 243 constantly contacts the test piece T.

The center axis of the needle 243 is arranged precisely at the X-axis reference point of the second movable part 40, so that displacement in the radial direction of the outer circumferential surface at the central portion of the test piece T is measured. Since the configuration of the sensor support member 244 in the second radial direction displacement detection unit 240 and the relative arrangement relationship between the plate 241, the needle 243, the sensor support member 244, the liner guide 248 and the contact-type displacement meter 250 are the same as the configurations of the sensor support members 224a to 224c of the first radial direction displacement detection unit 220 and the arrangement relationship between the plate 221, the needles 223a to 223c, the sensor support members 224a to 224c, the liner guide 228 and the contact-type displacement meters 230a to 230c excepting that the direction of the measurement axis of the contact type displacement meter 250 is different, details of each part of the second radial direction displacement detection unit 240 are omitted.

Since the configuration of the third radial direction displacement detection unit 260 is a mirrored image of the second radial direction displacement detection unit 240, details of the configuration of the third radial direction displacement detection unit 260 are omitted.

In the axial force-internal pressure type circular tube bulge testing, the tube-like test piece T expands in the circumferential direction from the central portion in the span by the internal pressure of the tube-like test piece T. That is, the vertical cross section of the test piece T deforms in a shape of a bell having an apex at the central portion of the span. The strain of the test piece T in the circumferential direction is calculated based on the displacements of the test piece T in the outer circumferential direction of the test piece T at the central portion of the span measured principally by the first, second and the third radial direction displacement detection units 220, 240 and 260. It is possible to determine the strain in the circumferential direction of the test piece T based only on a displacement in the radial direction of a point on the outer circumferential surface of the test piece T in the central portion in the span measured, for example, by using the third radial direction displacement detection unit 260. However, in this embodiment, it is possible to measure more precisely the displacements in the radial direction on the outer circumferential surface of the test piece T by the first, second and third radial direction displacement detection units 220, 240 and 260, and to measure more precisely the strain in the circumferential direction of the test piece T by using three measurements obtained at points arranged in the same intervals of 120° around the center axis of the test piece T. Furthermore, as described above, the first radial direction displacement detection unit 220 includes three displacement meters arranged to have the same intervals in the center axis direction of the test piece T. As a result, curvature of deformation in a shape of a bell of the test piece T in the vertical cross section is determined, and thereby it becomes possible to precisely measure the strain of the test piece T in the circumferential direction.

Figure 8:
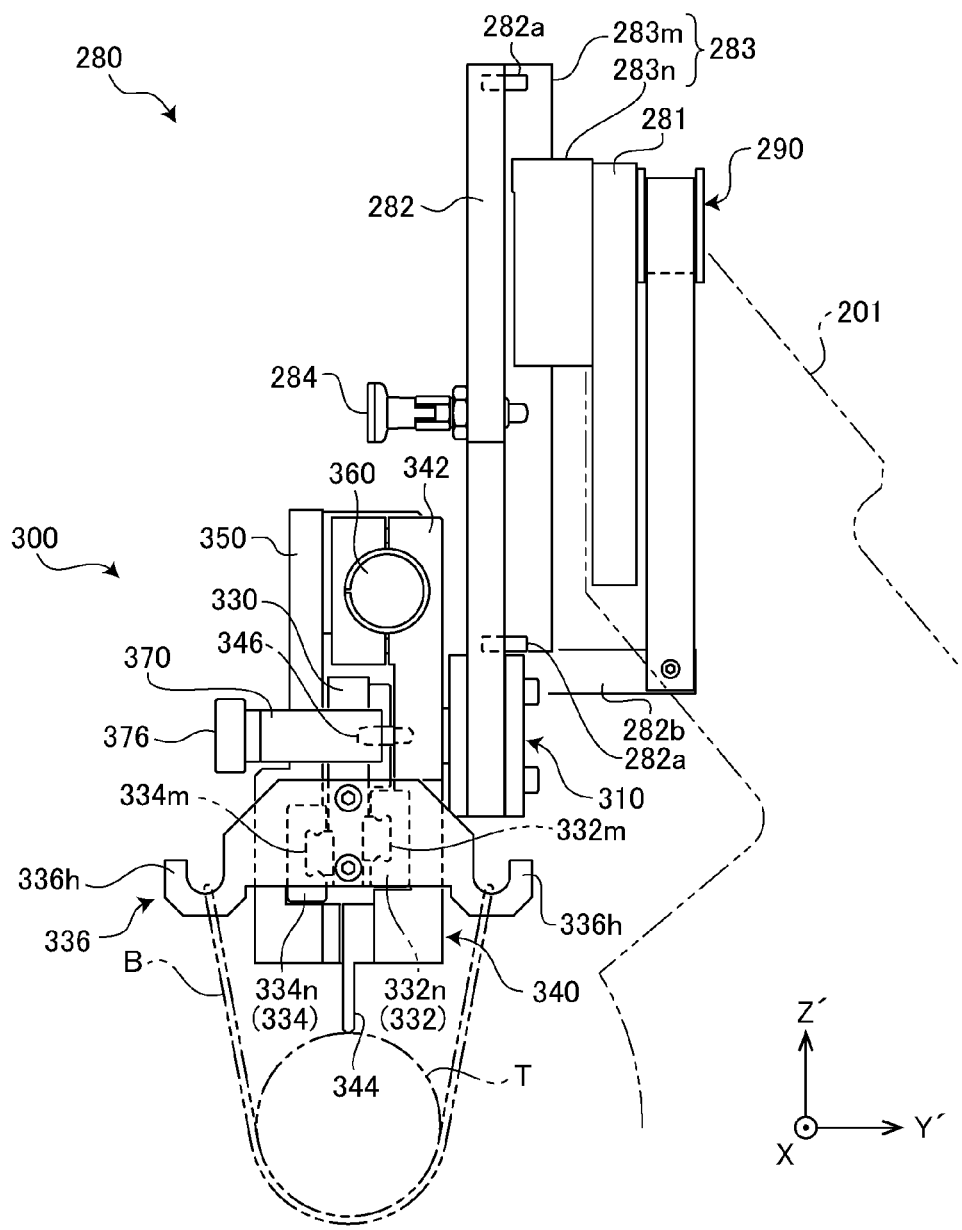
FIG. 8 is a side view of an axis direction displacement detection unit.
Figure 9:
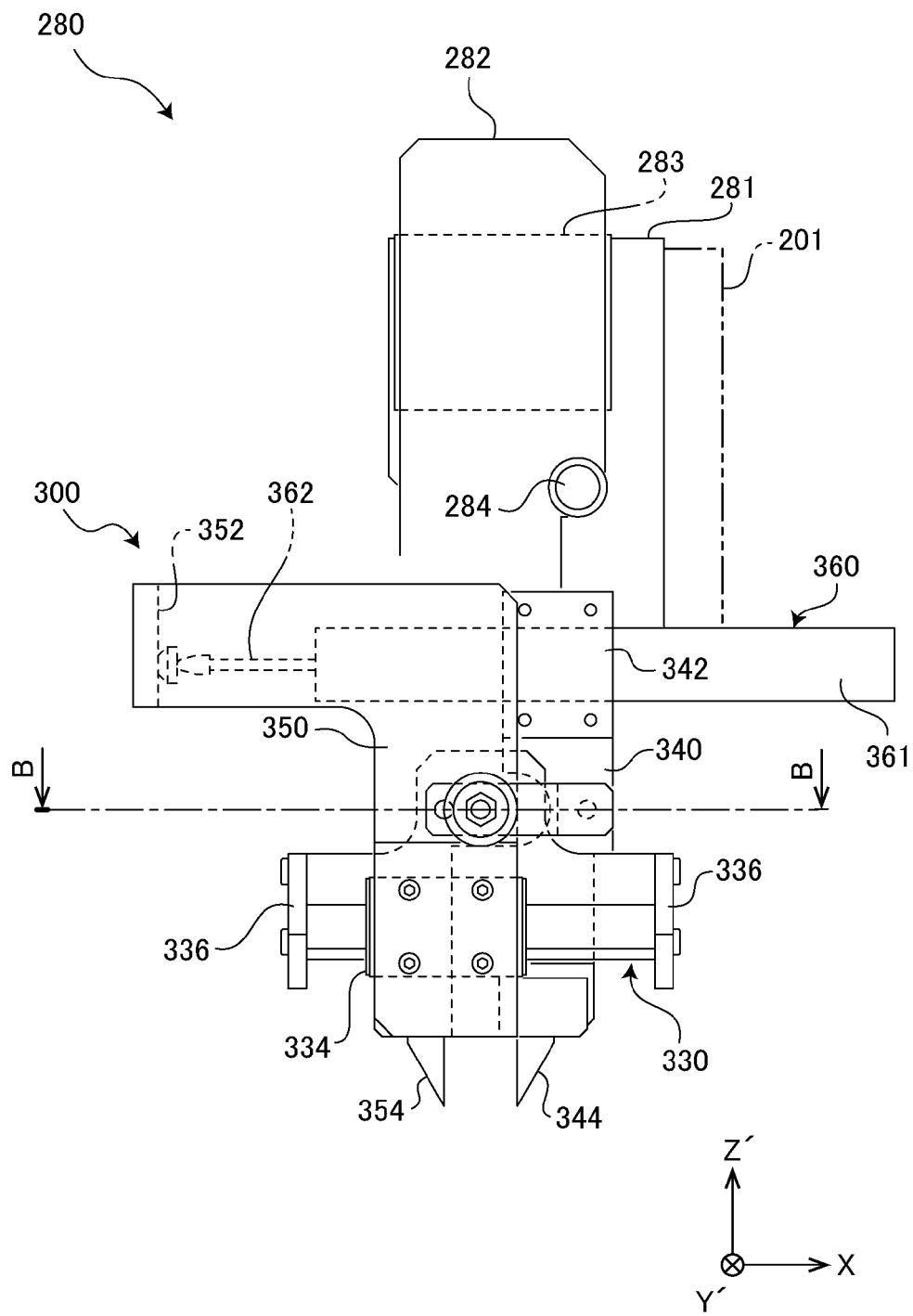
FIG. 9 illustrates the axis direction displacement detection unit viewed along a Y'-axis direction.
Figure 10:
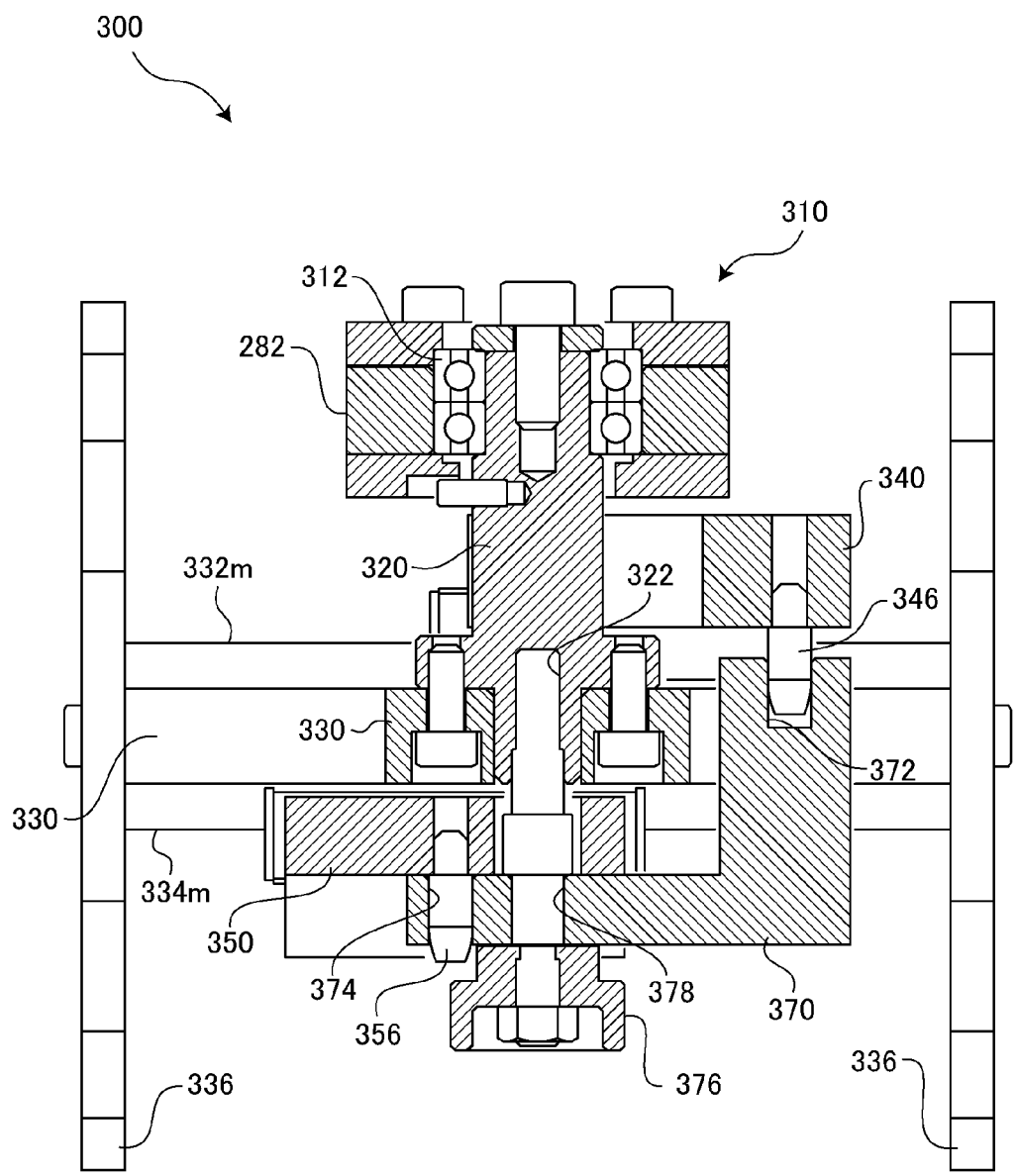
FIG. 10 is a cross sectional view taken in the direction of an arrow B-B in FIG. 9.

Next, the configuration of the axis direction displacement detection unit 280 is explained. The axis direction displacement detection unit 280 detects extension of in the center axis direction on the outer circumferential surface of the test piece T at the central portion of the span. FIG. 8 is a drawing illustrating the axis direction displacement detection unit 280 viewed in the negative direction of X-axis. Y'-axis and Z'-axis in FIG. 8 represent respectively coordinate axes defined by rotating Y-axis and Z-axis by 40° about X-axis as shown in FIG. 5. FIG. 9 as a drawing illustrating the axis direction displacement detection unit 280 viewed along the Y'-axis direction. FIG. 10 is a cross sectional view taken in the direction of an arrow B-B in FIG. 9. Each of FIGS. 8 to 10 illustrates a situation where a setting jig 370 used to set the axis direction displacement detection unit 280 to an initial state when the axis direction displacement detection unit 280 is attached to the test piece T. The testing is performed in the state where the setting jig 370 is removed.

The axis direction displacement detection unit 280 includes a plate 281 perpendicularly fixed to the plate 201, and a movable plate 282 arranged to be parallel with the plate 281. On a surface of the movable plate 282 facing the plate 281, a rail 283m is fixed to extend in the Z-axis direction. On a surface of the plate 281, a runner block 283n is fixed to engage with the rail 283m. That is, the movable plate 282 is attached to the surface (the surface on the negative side of Y'-axis) of the plate 281 via a linear guide 283 constituted by the rail 283m and the runner block 283n, and is slidable with respect to the plate 281 in the Z-axis direction. As a result, even when the outer circumferential surface of the test piece T shifts toward the axis direction displacement detection unit 280 (in the radial direction) due to expansion of the test piece T, the axis direction displacement detection unit 280 also moves smoothly in the radial direction in accordance with the displacement of the test piece T. Accordingly, it becomes possible to stably continue measurement of the displacement of the test piece T by the axis direction displacement detection unit 280 without causing unnecessary stress to the axis direction displacement detection unit 280 and the test pieces T. To the movable plate 282, a hand-tightening screw 284 that engages with a female screw provided on an attachment surface of the rail 283m is rotatably attached. To a surface of the movable plate 282 facing the plate 281, a plurality of positioning pins 282a that engage with positioning shapes (notches) formed on the attachment surface of the rail 283m are attached. The movable plate 282 is detachably attachable to the rail 283m with a high degree of precision by the positioning pin 282a and the hand-tightening screw 284. When the test piece T is replaced, the movable plate 282 is detached from the rail 283 by loosening the hand-tightening screw 284 in order to secure a space required for replacement of the test piece T.

At the tip portion of the movable plate 282 in the negative direction of Z-axis, a bearing part 310 (FIG. 10) which supports a body part 300 of the axis direction displacement detection unit 280 to be able to swing about Y'-axis is provided. The body part 300 includes a shaft 320, a plate 330, a first sliding part 340, a second sliding part 350, and a contact-type displacement meter 360. The contact-type displacement meter 360 has the same configuration as that of the contact-type displacement meters 230a to 230c. One end of the shaft 320 extending in the Y'-axis direction is rotatably supported by a multi-row ball bearing 312 provided in the bearing part 310. To the other end of the shaft 320, the plate 330 is perpendicularly fixed. That is, the plate 330 arranged to be parallel with the movable plate 282 is supported by the shaft 320 and the bearing part 310 to be able to swing about Y'-axis with respect to the movable plate 282. With this configuration, when the test piece T deforms largely due to, for example, buckling, the axis direction displacement detection unit 280 can be prevented from being damaged by receiving an excessively large degree of load from the test piece T because the body part 300 swings smoothly in accordance with deformation of the test piece T. Furthermore, with this configuration, the axis direction displacement detection unit 280 does not hamper movement of the test piece T when the test piece T is attached to the material testing machine 1, and therefore the test piece T can be attached/detached even in the state where the axis direction displacement detection unit 280 is attached.

The plate 330, the first sliding part 340 and the second sliding part 350 are arranged to be parallel with each other, and a part of the plate 330 is sandwiched between the first sliding part 340 and the second sliding part 350. The first sliding part 340 and the second sliding part 350 are attached to the plate 330 via the linear guides 332 and 334, respectively, and are able to slide in a predetermined direction (X-axis direction in FIGS. 8 and 9) with respect to the plate 330. Specifically, a rail 332m of the linear guide 332 and a rail 334m of the linear guide 334 are respectively attached to both sides of the plate 330. Furthermore, a runner block 332n of the linear guide 332 is attached to the first sliding part 340, and a runner block 334n of the linear guide 334 is attached to the second sliding part 350.

At ends (ends on the negative side of Z-axis in FIGS. 8 to 10) of the first and second sliding parts 340 and 350, jaws 344 and 354 that contact a side of the test piece T are provided. At the other end of the first sliding part 340, a clamp 342 for fixing a body part 361 of the contact-type displacement meter 360 is provided. The contact-type displacement meter 360 is arranged so that a measurement axis (an axis direction of a contact 362) becomes parallel with the movement direction of the liner guides 332 and 334. At the other end of the second sliding part 350, a stopper plate 352 which is perpendicular to the contact 362 is provided. When the jaws 344 and 354 move relatively in the measurement axis direction (X-axis direction in FIGS. 8 to 10), the stopper plate 352 of the second sliding part 350 moves in the measurement axis direction with respect to the body part 361 of the contact-type displacement meter fixed to the first sliding part 340. Since the contact 362 of the contact-type displacement meter is pressed in a protruding direction (a negative direction of X-axis) by a coil spring (not shown) provided in the body part 361, the contact 362 moves in the X-axis direction in accordance with movement of the stopper plate 352 while maintaining the state where the tip of the contact 362 contacts the stopper plate 352. As a result, the relative displacement between the jaws 344 and 354 is detected by the contact-type displacement meter 360.

A hook plate 336 is attached to both ends in the measurement axis direction of the plate 330. At both ends in Y'-axis direction of the hook plate 336, hooks 336h are formed. As shown in FIG. 8, during the testing, a rubber band B is hooked to the both hooks 336 in the state where the tips of the jaws 344 and 354 contact the test piece T, so that the test piece T is sandwiched between the rubber band B and the body part 300 of the axis direction displacement detection unit 280. As a result, the jaws 344 and 354 are pressed against the side surface of the test piece T by an elastic force of the rubber band B. Therefore, the jaws 344 and 354 move in accordance with displacement of the test piece T in the axis direction without slipping on the side surface of the test piece T, and the displacement in the axis direction is precisely detected.

The body part 300 of the axis direction displacement detection unit 280 is able to swing about the axis 320. Therefore, even when the test piece T has warpage or a difference is caused between the distance from the tip of the jaw 344 to the test piece T and the distance from the tip of the jaw 354 to the test piece T due to ununiform deformation caused in the test piece T with respect to the central portion in the span, the difference in distance is canceled by rotation of the body part 300 and the two jaws 344 and 354 securely contacts the side surface of the test piece T. As a result, it becomes possible to measure displacement of the test piece T in the axis direction securely and constantly.

As shown in FIG. 10, on the surfaces of the first and second sliding parts 340 and 350 facing the setting jig 370, positioning pins 346 and 356 are provided, respectively. Furthermore, along a center axis of the surface of the shaft 320 facing the setting jig 370, a female screw 322 is formed to engage with the hand-fastening screw 322. In the setting jig 370, holes 372 and 372 respectively engaging with the positioning pins 346 and 356 are formed, and a through hole 378 into which the hand-fastening screw 322 is inserted are formed. By inserting the positioning pins 346 and 356 into the holes 372 and 372 of the setting jig 370 and by screwing the hand-fastening screw 322 into the female screw 322 via the through hole 378 of the setting jig 370, the setting jig 370 is attached to the body part 300 of the axis direction displacement detection unit 280. At this time, the shaft 320, the plate 330 fixed integrally to the shaft 320, the first sliding part 340, the second sliding part 350 and the setting jig 370 are fixed in a predetermined arrangement relationship. Furthermore, at this time, the interval between the center axis of the shaft 320 and the tip of the jaw 344 in X-axis direction and the interval between the center axis of the shaft 320 and the jaw 354 are set to a common, predetermined value (10 mm in this embodiment). The center axis of the shaft 320 is arranged just above the center line of the base 41 in X-axis direction. That is, the shaft 320 is positioned at the intermediate point in X-axis direction between the movable chuck 32 and the fixed chuck 52. Therefore, in the state where the setting jig 370 is attached, the jaws 344 and 354 are arranged at positions which are away from each other by the same distance from the center of the span of the test piece T in the positive direction and the negative direction of X-axis. When the axis direction displacement detection unit 280 is attached to the test piece T in the state where the setting jig 370 is attached, the jaws 344 and 354 can be fixed while letting the jaws 344 and 354 to contact the outer circumferential surface of the test piece T to have a predetermined interval in the central portion of the span of the test piece T.

Figure 11:
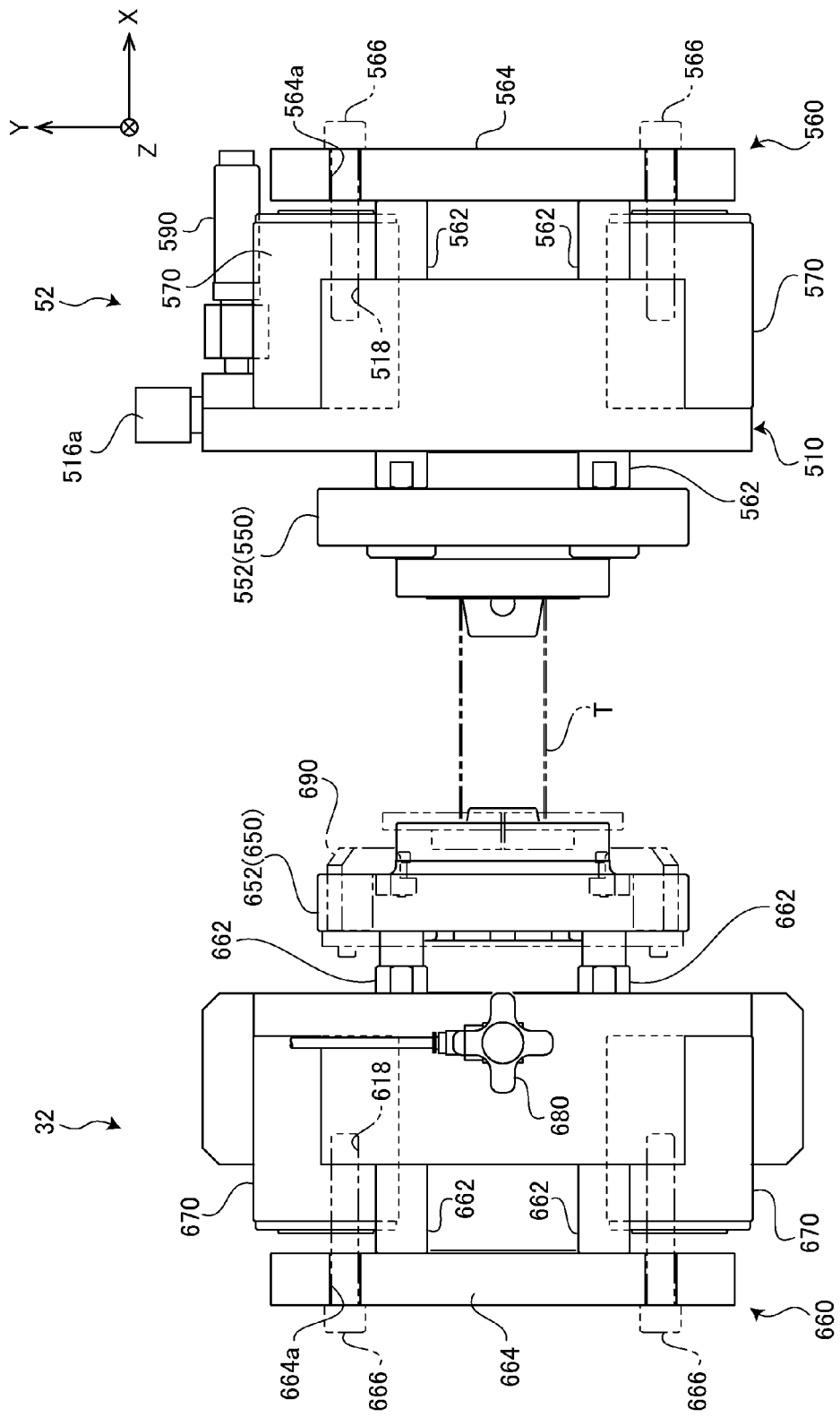
FIG. 11 is a top view of a fixed chuck and a movable chuck.
Figure 12:
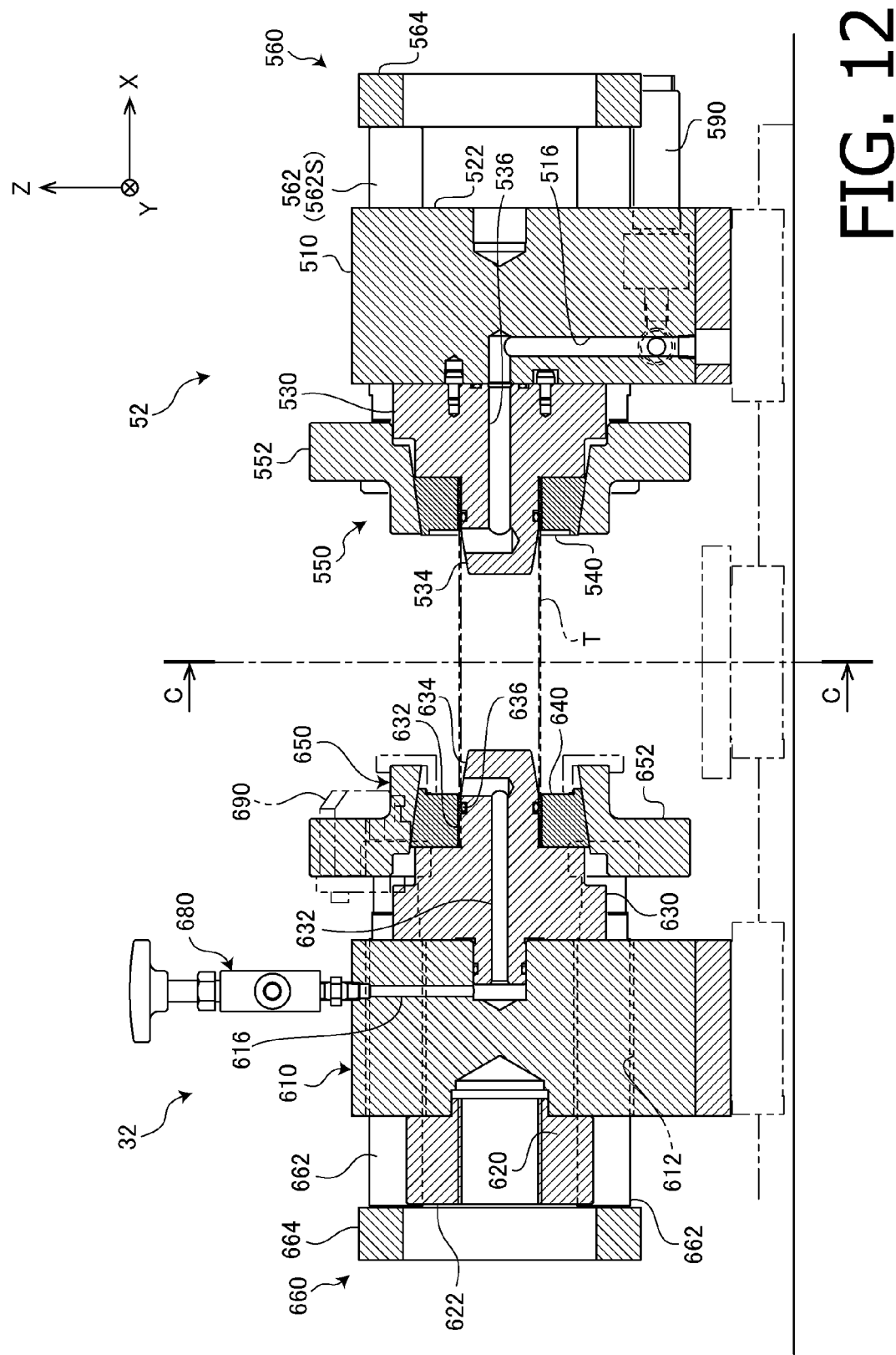
FIG. 12 is a vertical cross section of the fixed chuck and the movable chuck.

Next, details of the chucks 32 and 52 are explained. FIGS. 11 and 12 respectively show a top view and a vertical cross section of the chucks 32 and 52. In FIGS. 11 and 12, the right side chuck 52 is in a clamping state and the left side chuck 32 is in an unclamping state. The chuck 32 includes a support block 610, a flange part 620, a core 630, a collet 640, a sleeve 650, a slider 660, and two oil pressure cylinders 670 (FIG. 11). The slider 660 includes four rods 662 and a joint plate 664. The flange part 620 is attached to the negative side surface in the X-axis direction of the support block 610, and the core 630 is attached to the positive side surface in the X-axis direction of the support block 610. In the support block 610, four through holes 612 extending in the X-axis direction are formed. Each through hole 612 has an inner diameter slightly larger than an outer diameter of the rod 662, and the rods 662 are slidably inserted into the through holes 612, respectively. Ends of the four rods 662 on the negative side in the X-axis direction are fixed to the joint plate 664. The oil pressure cylinder 670 is configured to be able to push the test piece T and the joint plate 664 toward the negative side in the Y-axis direction. The flange part 620 is a structural part for attaching the joint member 33, and a flange attachment surface 622 in which a screw hole not shown is formed is provided at one end of the flange part 620. At the tip of the core 630, a cylinder part 632 having a diameter slightly smaller than an inner diameter of the test piece T is provided. Adjacent to the tip side of the cylinder part 632, a tapered part 634 formed such that an outer circumferential surface becomes smaller at a point closer to the tip side is provided. At the tip side on the outer circumferential surface of the cylinder part 632, a ring-shaped groove 636 to which an O-ring is attached is formed. The collet 640 is a ring-shaped member, and four notches (not shown) radially extending from the center axis are formed on the collet 640. The collet 640 is divided into four blocks by the four notches, excepting the inner circumferential end on the support block 610 side, and each divided piece is movable in the radial direction. The inner circumferential surface of the collet 640 is formed as a cylindrical surface having a diameter slightly larger than an outer diameter of the test piece T, and is arranged to cover the cylinder part 632 of the core 630. During the testing, the test piece T is sandwiched between the inner circumferential surface of the collet 640 and the cylinder part 632 of the core 630. The outer circumferential surface of the collet 640 is formed as a conic surface (a tapered surface) which becomes thinner toward the tip. The inner circumferential surface of the sleeve 650 is also formed as a conic surface having the same tapering angle as that of the outer circumferential surface of the collet 640, and the sleeve 650 is arranged to cover the collet 640. On the support block 610 side of the sleeve 650, a flange part 652 is formed to protrude outward in the radial direction.

The chuck 52 includes a support block 510, a core 530, a collet 540, a sleeve 550, a slider 560 and two oil pressure cylinder 570 (FIG. 11). The collet 540, the sleeve 550, the slider 560 and the oil pressure cylinder 570 have the same configurations as those of the collet 640, the sleeve 650, the slider 660 and the oil pressure cylinder 670 of the chuck 32, respectively. The core 530 also has the same configuration as that of the core 630 of the chuck 32, excepting the shape of the fixed part with respect to the support block 510 and a detailed structure of a duct line 514 which is described later. On the positive side surface in X-axis direction of the support block 510, a flange attachment surface 522 in which a screw hole (not shown) for fixing the joint member 53 is formed is provided. On a surface of the support block 510 on the negative side in X-axis direction, the core 530 is attached. In the support block 510, four through holes 512 are formed to extend in X-axis direction, and rods 562 of the slider 560 are respectively inserted into the through holes 512.

Figure 13:
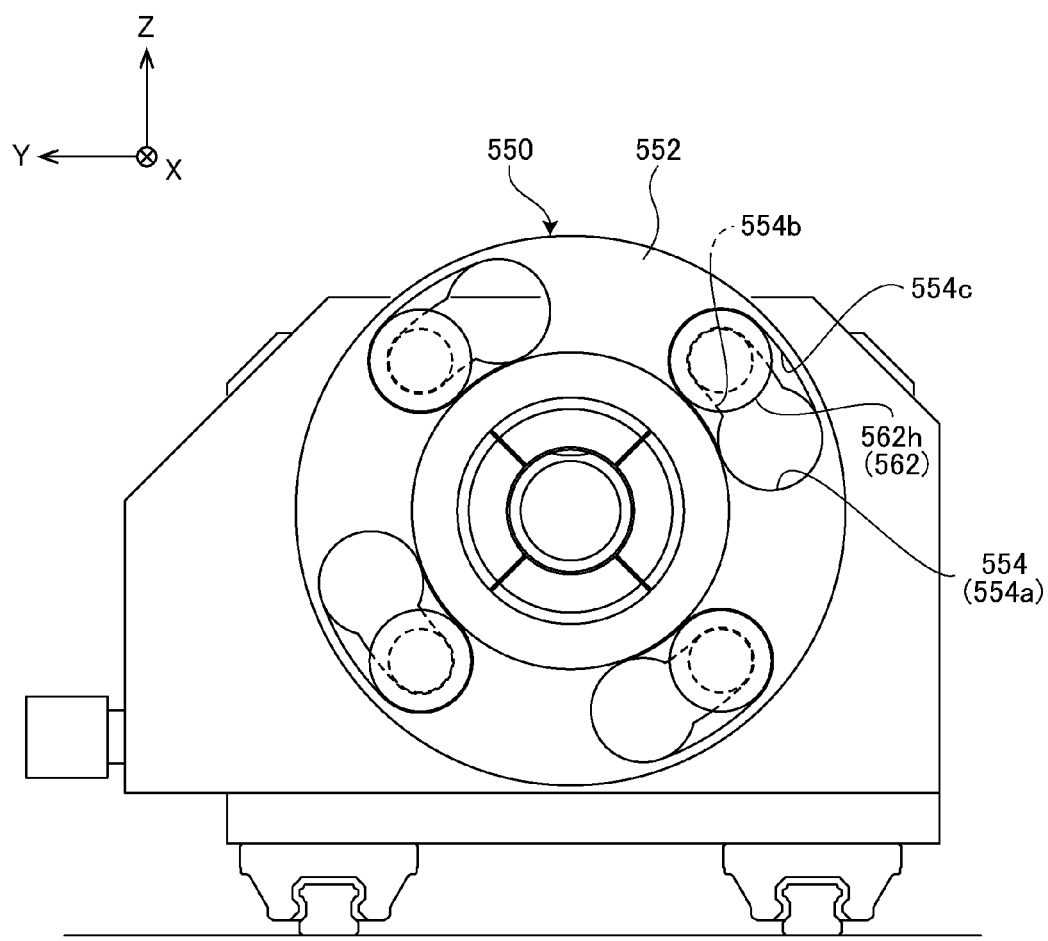
FIG. 13 is a drawing taken in the direction of an arrow C-C in FIG. 12.

FIG. 13 is a drawing taken in the direction of an arrow C-C in FIG. 12. In the flange part 552 of the sleeve 550, four through holes 554 are formed to extend in the X-axis direction. The through hole 554 has an insertion part 554a into which a head 562h of the rod 562 can be inserted, and a narrow gap part 554b extending along the circumferential direction (in the counterclockwise direction in FIG. 13) from the insertion part 554a. On a surface of the flange part 552 facing the chuck 32, a counter boring 554c is formed around the narrow gap part 554b. By inserting the rod 562 into the through hole 554 of the flange part 552 and then rotating the sleeve 550 in the clockwise direction, the head 562h of the rod 562 engages with the counter boring 554c of the flange part 552 and it becomes impossible to pull out the rod 562 from the flange part 552 even when the rod 562 is driven in the X-axis direction.

In the support block 610 and the core 630 of the chuck 32, duct lines 616 and 636 which supply a working fluid for applying an internal pressure to the test piece T are formed. In the support block 510 and the core 530 of the chuck 52, duct lines 516 and 536 which supply a working fluid for applying an internal pressure to the test piece T are formed. As a working fluid, a working oil or water mixed with a rust preventive agent is used. An end (a nipple 516a) of the duct line 516 of the support block 510 is connected to a liquid pressure source not shown, and the other end of the duct line 516 is connected to one end of the duct line 532 formed in the core 530. At a midway point of the duct line 516, an oil pressure meter 590 is provided. The other end of the duct line 532 of the core 530 is opened toward the outer circumferential surface of a tapered part 534, and the working fluid is poured into the inside of the test piece T via the opening of the duct line 532. One end of the duct line 616 formed in the support block 610 of the chuck 32 is connected to a valve 680 for releasing air, and the other end of the duct line 616 is connected to an end of the duct line 636 of the core 630. An outlet of the valve 680 is connected to a working fluid tank not shown. The other end of the duct line 636 of the core 630 is opened to the outer circumferential surface of the tapered part 634, and the working oil in the tube of the test piece T flows into the duct lines 636 and 616 via this opening.

When the test piece T is clamped by the chuck 52, one end of the test piece T is inserted into a cylinder part 532 of the core 530, the collet 540 is attached to the outer circumferential part of the test piece T, and then the sleeve 550 is attached to the outer circumferential part of the collet 540. When the sleeve 550 is attached, the rod 562 is inserted into the through hole 554 (FIG. 13) of the flange part 552, and the head 562h of the rod 562 is engaged with the counter boring 554c of the flange part 552 by rotating the sleeve 550 in the clockwise direction. Similarly, the other end of the test piece T is attached to the chuck 32. Since the test piece T closely contacts the cylinder parts 532 and 632 by the O-rings 536 and 636 by inserting the both ends of the test piece T into the cylinder part 532 of the core 530 and the cylinder part 632 of the core 630, the working oil is prevented from leaking through a gap between the test piece T and the cores 530 and 630 even when the working oil is supplied. Next, when the working fluid is supplied from the liquid pressure source at a low pressure by opening the valve 680, the working fluid is sent out to the working oil tank via the duct lines 516 and 536, the test piece T, the duct lines 636 and 616 and the valve 680. At this time, air in the test piece T and the duct lines 516, 536, 636 and 616 is ejected to the working oil tank together with the working fluid, and the ducts lines 516, 536, 636 and 616 are filled with the working oil. Next, when a predetermined initial liquid pressure is supplied by the liquid pressure source by closing the valve 680, the oil pressure cylinder 570 (670) operates, and by driving the joint plate 564 (664) to the positive direction (negative direction) of X-axis, the sleeve 550 (650) is also strongly pushed to the positive direction (negative direction) of X-axis via the rod 562 (662) fixed to the joint plate 564 (664). The collet 540 (640) is strongly pushed inward by the tapered surface of the sleeve 550 (650), and the test piece T is firmly clamped between the cylinder part 532 (632) of the core 530 (630) and the collet 540 (640). When the pressure of the working fluid is released after the testing, the fastened state of the collet 540 (640) by the rod 562 (662) and the sleeve 550 (650) is released, and the state of the collet 540 (640) is brought to an unclamped state. Female screws 518 (618) which engage with unclamp bolts 566 (666) are formed on the support block 510 (610), and through holes 564a (664a) into which the unclamp bolts 566 (666) are inserted are formed in the joint plate 564 (664). When the sleeve 550 (650), the collet 540 (640) and the test piece T are fixed and are brought to the state where the clamped state is not released, the fixing of the collet 540 (640) is cancelled and the collet 540 (640) can be brought to the unclamped state by inserting the unclamp bolts 566 (666) into the though holes 664a (664a) to screw in the female screws 518 (618) and by pushing the joint plate 564 (664) to the support block 510 (610) side.

Hereafter, a method for calculating the strain and stress of the test piece T by the control unit (not shown) based on detection results of the displacement of the test piece T by the sensor unit 200 is explained. In the circular tube bulge testing, the stress and the strain in the circumferential direction (θ) and the tube axis direction (φ) of the tube-like test piece T are measured. The circumferential direction stress $\sigma_\theta$ and the tube axis direction stress $\sigma_\phi$ of the test piece T are calculated by the expressions (1) and (2), respectively. The circumferential direction strain $\epsilon_\theta$ and the tube axis direction strain $\epsilon_\phi$ of the test piece T are calculated by the expressions (3) and (4), respectively. The wall thickness t of the test pieces T is calculated by the expression (5).

$$\sigma_\phi = \frac{P\pi(D/2 - t)^2 + T}{\pi(D - t)t} \tag{1}$$

$$\sigma_\theta = \frac{(R_\phi - t)(D - 2t)}{(2R_\phi - t)t}P - \frac{D - t}{2R_\phi - t}\sigma_\theta \tag{2}$$

$$\varepsilon_\phi = \ln\left(\frac{2R_\phi}{L_0}\sin^{-1}\left(\frac{L}{2R_\phi}\right)\right) \tag{3}$$

$$\varepsilon_\theta = \ln\left(\frac{D}{D_0}\right) \tag{4}$$

$$t = t_0 \cdot \exp(\varepsilon_\phi - \varepsilon_\theta) \tag{5}$$

$$L = L_0 + e_6 \tag{6}$$

where,

P: inner pressure (liquid pressure)

D: outer diameter of test piece T ($D_0$: initial value)

t: wall thickness of test piece T ($t_0$: initial value)

T: load in tube axis direction $R_\phi$: curvature radius in tube axis direction L: distance between sample points ($L_0$: initial value)

$e_6$: displacement in axis direction of outer circumferential surface in central portion of span of test piece T (detection value of axis direction displacement detection unit).

The inner pressure P is detected by a liquid pressure gauge provided in the liquid pressure source (not shown). The stress T in the tube axis direction is detected by a load cell 54. The outer diameter D and the curvature radius $R_\phi$ in the tube axis direction of the test piece T are obtained by a method described below.

(Method for Obtaining Outer Diameter D)

The outer diameter D is calculated based on displacements $e_1$, $e_2$ and $e_3$ in the radial direction of the outer circumferential surface at the central portion of the span (the X-axis reference point) of the test piece T, detected by the first radial direction displacement detection unit 220 (the contact type displacement meter 230b), the second radial direction displacement detection unit 240 and the third radial direction displacement detection unit 260, respectively. Specifically, the outer diameter D of the test piece T is calculated by the following expression (7) by defining an average of the three displacement measurement values $e_1$, $e_2$ and $e_3$ as a displacement amount of the radius of the test piece T.

$$D = D_0 + 2 \cdot \left(\frac{e_1 + e_2 + e_3}{3}\right) \tag{7}$$

Since the test piece T does not have a complete axial symmetry, the deformation of the test piece T also becomes slightly asymmetrical. Therefore, when change of the outer diameter of the test piece T is measured only in one direction, an error of the outer diameter D becomes relatively large, and the test precision (i.e., precision of the finally obtained circumferential direction stress $\sigma_\theta$ and the tube axis direction stress $\sigma_\phi$) decreases. In this embodiment, by calculating the outer diameter D from the average of the displacements in the radial direction of the outer circumferential surface measured at three points along the circumferential direction in the central portion of the span of the test piece T, the measurement precision of the outer diameter D of the test piece T increases, and thereby it becomes possible to measure the circumferential direction stress $\sigma_\phi$ and the tube axis direction stress $\sigma_\theta$ with a high degree of precision. Furthermore, since the first, second and third radial direction displacement detection units 220, 240 and 260 are arranged to have the same intervals around the tube axis of the test piece T, the average of the displacement measurement values $e_1$, $e_2$ and $e_3$ by the three radial direction displacement detection units becomes a value close to an average of displacements of the whole circumference. That is, according to the embodiment, it becomes possible to effectively decrease a measurement error with a small number of radial direction displacement detection units.

(Method for Obtaining Tube Axis Direction Curvature Radius $R_\phi$)

The tube axis direction curvature radius $R_\phi$ is calculated by the expressions (8) and (9) based on displacements $e_4$, $e_1$ and $e_5$ of the needle 223a to 223c detected by the three contact-type displacement meters 230a to 230c of the first radial direction displacement detection unit 220. A Sign of each of the displacements $e_1$ to $e_5$ is defined such that a displacement in the direction that the radius of the test piece T increases is positive.

$$R_\phi = \frac{h^2 + (S/2)^2}{2h} \tag{8}$$

$$h_\phi = \frac{(e_1 - e_4) + (e_1 - e_5)}{2h} \tag{9}$$

where,

S: arrangement interval between needles 223a to 223c of first radial direction displacement detection unit 220.

The foregoing is the exemplary embodiment of the invention. The configuration of the embodiment of the invention is not limited to one explained above, and can be varied within the technical concept expressed in the claims. That is, another embodiment of the invention is not necessarily provided with all the above described features, but may be configured to be provided with another feature additionally or alternatively.

In the above described embodiment, the other end of the link 142 whose one end is coupled to the second movable part 40 is coupled to the link 143 at the central portion of the link 143. However, the other end of the link 142 may be coupled to the link 141 at the central portion of the link 141. Furthermore, two links 142 may be provided, and the other end of one of the links 142 may be coupled to the link 141 and the other end of the other of the links 142 may be coupled to the link 143. In this case, since the second movable part 40 is driven by the two links 142, it becomes possible to move the measurement unit smoothly and precisely even when a measurement unit having a heavy weight is used.

In the above described embodiment, the strain at the central portion of the test piece T is measured; however, the present invention may be applied to the case where measurement is performed in regard to items other than the shape at the central portion of the test piece T. As to the measurements other than the shape for which the invention can be used, an electric property (e.g., a resistance f the test piece T) or an optical property (e.g., optical reflectivity) can be cited.

In the above described embodiment, the link length of the link 142 is defined as a half of the link length of the link 143, and the second movable part 40 is positioned at the intermediate point between the first movable part 30 and the fixed part 50. However, the ratio between the link length of the link 142 and link length of the link 143 (i.e., the similarity scaling factor between the isosceles triangle 578 and the isosceles triangle 679) may be defined arbitrarily.

In the above described embodiment, an oil pressure actuator is controlled and driven as an actuator by a servo valve is used; however, another type of actuator (e.g., a motor-driven and oil pressure actuator driven and controlled by a servo motor, or a motor-driven actuator driven by various types of motors) may be used.

In a conventional method where change of an cross sectional shape at a central portion in a lengthwise direction of a test piece is measured by a CCD camera or a sensor array, only a measurement precision lower than an arrangement interval of a light-receiving device is obtained, and it was impossible to detect a minute change. Furthermore, since the measurement precision is decreased by a special angle or diffraction of projected light and a projection length becomes long when a large test piece is used, it was impossible to perform measurement with a high degree of precision. By contrast, according to the embodiment of the invention described above, since a contact-type displacement meter is used, it becomes possible to perform measurement with an extremely higher degree of precision and an extremely higher degree of reliability, and therefore it becomes possible to perform measurement with an adequate degree of precision even when testing is performed for a large test piece T. It should be noted that a displacement meter (e.g., a laser reflection type non-contact-type displacement meter) which is able to measure a local displacement with a high degree of precision and with a high degree of reliability, other than a contact-type displacement meter, may be used.

The above described sensor unit movement mechanism may be used various types of measurement including a mechanical test (e.g., a tensile test, a compressive test or a torsion test), without limiting to the circular tube bulge test.

What is claimed is:

1. A material testing machine measuring strain of a tube-like test piece by applying inner pressure and stress in a tube axis direction to the test piece, comprising:
  a plurality of radial direction displacement detection units that detect displacements of an outer circumferential surface of the test piece in a radial direction in a central portion of an effective length of the test piece;
  an axis direction displacement detection unit that detects a displacement in the tube-axis direction of the outer circumferential surface of the test piece in the central portion of the effective length of the test piece; and
  a calculation unit that calculates the strain in a circumferential direction and the tube-axis direction of the test piece in the central portion of the effective length, based on detection results by the plurality of radial direction displacement detection units and the axis direction displacement detection unit, wherein:
  the plurality of radial direction displacement detection units respectively detect displacements at different directions around the tube axis of the test piece;
  each of plurality of radial direction displacement detection units comprises a first displacement meter that detects a displacement in the radial direction of the outer circumferential surface of the test piece in the central portion of the effective length;
  at least one of the plurality of radial direction displacement detection units comprises a second displacement meter that is aligned with the first displacement meter in the tube axis direction and detects a displacement in the radial direction of the outer circumferential surface of the test piece; and
  each of the first and second displacement meters comprises:
    a needle that has a tip arranged to perpendicularly contact the outer circumferential surface of the test piece and is provided to be able to move in the radial direction in accordance with the displacement in the radial direction of the outer circumferential surface of the test piece;
    a fixed frame;
    a movable frame that is provided to be able to move in the radial direction of the test piece with respect to the fixed frame; and
    a displacement sensor that has a body part attached to the movable frame and a contact that protrudes from an end of the body part in the radial direction of the test piece in a retractable manner,
  wherein:
  a tip of the contact of the displacement sensor is arranged to contact a stopper plate provided on the fixed frame;
  the needle is arranged such that a lengthwise direction is oriented in the radial direction of the test piece;
  the needle is attached to the movable frame such that the needle protrudes from an end of the movable frame facing the test piece;
  the displacement in the radial direction of the circumferential surface of the test piece is detected by detecting a moving amount of the needle; and
  the calculation unit calculates a curvature radius in the tube axis direction of the outer circumferential surface of the test piece in the central portion of the effective length, based on detection results by the first and second displacement meters of the at least one of the plurality of radial direction displacement detection units.

2. The material testing machine according to claim 1, wherein the plurality of radial direction displacement detection units comprise first, second and third radial direction displacement detection units arranged around the tube axis of the test piece at intervals of 120°.

3. The material testing machine according to claim 1, further comprising a sensor unit moving mechanism that moves a sensor unit, in which the plurality of radial direction displacement detection units and the axis direction displacement detection unit are provided, in the tube axis direction of the test piece with respect to a device frame of the material testing machine,
the sensor unit moving mechanism comprising:
a first movable part that is provided to be able to move in the tube axis direction of the test piece with respect to the device frame and comprises a movable chuck which fixes one end of the test piece;

a fixed part that is fixed to the device frame and comprises a fixed chuck which fixes the other end of the test piece;

a second movable part that is arranged between the first movable part and the fixed part and moves the sensor unit in the tube axis direction of the test piece with respect to the device frame;

an actuator that is fixed to the device frame and moves the first movable part in the tube axis direction; and a link mechanism that couples the device frame, the first movable part and the second movable part with each other, and moves a central measuring device to a midway point between the movable chuck and the fixed chuck in accordance with movement of the first movable part.

4. A material testing machine measuring a response of a test piece by applying a stress to the test piece in a predetermined direction, comprising:

a device frame;

a first movable part that is provided to be able to move in the predetermined direction with respect to the device frame and comprises a movable chuck which fixes one end of the test piece;

a fixed part that is fixed to the device frame and comprises a fixed chuck which fixes the other end of the test piece;

a second movable part that is provided between the first movable part and the fixed part to be able to move in the predetermined direction with respect to the device frame and comprises a central measuring device which measures the response of the test piece in a central portion in the predetermined direction of the test piece when a load acts on the test piece;

an actuator that is fixed to the device frame and moves the first movable part in the tube axis direction;

a link mechanism that couples the device frame, the first movable part and the second movable part with each other, and keeps the central measuring device at a midway point of the test piece in the predetermined direction by moving the central measuring device to a midpoint between the movable chuck and the fixed chuck in accordance with movement of the first movable part; and a rail that extending in the predetermined direction, wherein:

the first movable part comprises a first runner block which engages with the rail, and is supported by the rail and the first runner block to be able to slide in the predetermined direction; and the second movable part comprises a second runner block that engages with the rail, and is supported by the rail and the second runner block to be able to slide in the predetermined direction.

5. The material testing machine according to claim 4, wherein:

the fixed part comprises:

a load sensor that measures a load acting on the test piece in the predetermined direction; and a third runner block that engages with the rail to be able to move in the predetermined direction, wherein the fixed chuck is located on the third runner block, and is fixed to the device frame via the load sensor.

6. The material testing machine according to claim 4, wherein the link mechanism comprises:

a first link whose one end is rotatably coupled to the first movable part via a first pin;

a second link whose one end is rotatably coupled to the second movable part via a second pin; and a third link whose one end is rotatably coupled to the device frame via a third pin arranged on an opposite side of the first pin with respect to the second pin, wherein:

the other end of the first link and the other end of the third link is rotatably coupled via a fourth pin;

the other end of the second link is rotatably coupled to one of the first link and the third link via a fifth pin;

an interval between the fourth pin and the first pin is equal to an interval between the fourth pin and the third pin; and an interval between the fifth pin and the second pin is equal to an interval between the fifth pin and one of the first pin and the third pin provided for one of the first link and the third link on which the fifth pin is provided.

7. The material testing machine according to claim 6, wherein:

the first movable part, the second movable part and the fixed part comprise base plates having lower surfaces on which the first, second and third runner blocks are attached, respectively;

the movable chuck, the central measuring device and the fixed chuck are respectively attached to upper surfaces of the base pates of the first movable part, the second movable part and the fixed part, and are respectively arranged above the base plates of the first movable part, the second movable part and the fixed part; and the link mechanism is attached to lower surfaces of the base plates and is located under the base plates.

8. The material testing machine according to claim 7, wherein:

the device frame comprises a plate having a horizontally oriented upper surface;

the rail is attached to the upper surface of the device frame;

the plate has a recessed part which is recessed in a horizontal direction by cutting off a central portion on a side of the plate, the recessed part having a bottom surface extending in parallel with and adjacent to the rail; and the first link and the third link are arranged in the recessed part.

9. A material testing machine measuring strain of a tube-like test piece by applying inner pressure and stress in a tube axis direction to the test piece, comprising:

a plurality of radial direction displacement detection units that detect displacements of an outer circumferential surface of the test piece in a radial direction in a central portion of an effective length of the test piece;

an axis direction displacement detection unit that detects a displacement in the tube-axis direction of the outer circumferential surface of the test piece in the central portion of the effective length of the test piece; and a calculation unit that calculates the strain in a circumferential direction and the tube-axis direction of the test piece in the central portion of the effective length, based on detection results by the plurality of radial direction displacement detection units and the axis direction displacement detection unit, wherein the plurality of radial direction displacement detection units respectively detect displacements at different directions around the tube axis of the test piece, wherein the axis direction displacement detection unit comprises:

a fixed plate;

a movable plate provided to be able to slide in a Z-axis direction with respect to the fixed plate; and a body unit that is provided at a tip portion in the Z-axis direction of the movable plate to be able to swing about a Y-axis, wherein the body unit comprises:

a plate attached to the movable plate to be able to swing;

a first sliding part that has a first jaw provided to contact a side of the test piece and is provided to be able to slide in the X-axis direction with respect to the plate;

a second sliding part that has a second jaw provided to contact a side of the test piece and is provided to be able to slide in the X-axis direction with respect to the plate; and a contact-type displacement meter that detects a relative displacement in the X-axis direction between the first jaw and the second jaw.

10. A material testing machine measuring a response of a test piece by applying a stress to the test piece in a predetermined direction, comprising:

a device frame;

a first movable part that is provided to be able to move in the predetermined direction with respect to the device frame and comprises a movable chuck which fixes one end of the test piece;

a fixed part that is fixed to the device frame and comprises a fixed chuck which fixes the other end of the test piece;

a second movable part that is provided between the first movable part and the fixed part to be able to move in the predetermined direction with respect to the device frame and comprises a central measuring device which measures the response of the test piece in a central portion in the predetermined direction of the test piece when a load acts on the test piece;

an actuator that is fixed to the device frame and moves the first movable part in the tube axis direction; and a link mechanism that couples the device frame, the first movable part and the second movable part with each other, and keeps the central measuring device at a midway point of the test piece in the predetermined direction by moving the central measuring device to a midpoint between the movable chuck and the fixed chuck in accordance with movement of the first movable part, wherein the link mechanism comprises:

a first link whose one end is rotatably coupled to the first movable part via a first pin;

a second link whose one end is rotatably coupled to the second movable part via a second pin; and a third link whose one end is rotatably coupled to the device frame via a third pin arranged on an opposite side of the first pin with respect to the second pin, wherein:

the other end of the first link and the other end of the third link is rotatably coupled via a fourth pin;

the other end of the second link is rotatably coupled to one of the first link and the third link via a fifth pin;

an interval between the fourth pin and the first pin is equal to an interval between the fourth pin and the third pin; and an interval between the fifth pin and the second pin is equal to an interval between the fifth pin and one of the first pin and the third pin provided for one of the first link and the third link on which the fifth pin is provided.

* * * * *